(12) United States Patent
Lu et al.

(10) Patent No.: US 7,268,157 B2
(45) Date of Patent: Sep. 11, 2007

(54) SUBSTITUTED ARYLALCANOIC ACID DERIVATIVES AS PPAR PAN AGONISTS WITH POTENT ANTIHYPERGLYCEMIC AND ANTIHYPERLIPIDEMIC ACTIVITY

(75) Inventors: Xian-Ping Lu, Quangdong (CN); Zhibin Li, Guangdong (CN); Chenzhong Liao, Guangdong (CN); Leming Shi, Guangdong (CN); Zhende Liu, Guangdong (CN); Baoshun Ma, Guangdong (CN); Zhiqiang Ning, Guangdong (CN); Song Shan, Guangdong (CN); Tuo Deng, Guangdong (CN)

(73) Assignees: Shenzhen Chipscreen Biosciences, Ltd., Shenshen, Guangdong (CN); Research Institute of Tsinghua University, Shenshen, Guangdong (CN)

( * ) Notice: Subject to any disclaimer, the term of this patent is extended or adjusted under 35 U.S.C. 154(b) by 233 days.

(21) Appl. No.: 10/715,622

(22) Filed: Nov. 18, 2003

(65) Prior Publication Data
US 2004/0142921 A1    Jul. 22, 2004

Related U.S. Application Data

(60) Provisional application No. 60/469,368, filed on May 9, 2003, provisional application No. 60/429,221, filed on Nov. 26, 2002.

(51) Int. Cl.
| | | |
|---|---|---|
| A61P 3/00 | (2006.01) | |
| A61K 31/403 | (2006.01) | |
| C07D 209/82 | (2006.01) | |

(52) U.S. Cl. ..................... 514/411; 548/444
(58) Field of Classification Search ............. 514/411; 548/444
See application file for complete search history.

(56) References Cited

U.S. PATENT DOCUMENTS

| 6,054,453 A | 4/2000 | Lohray et al. ............ 514/226.2 |
| 6,353,018 B1 | 3/2002 | Jeppesen et al. ............ 514/437 |
| 2003/0055076 A1* | 3/2003 | Jeppesen et al. ............ 514/290 |

FOREIGN PATENT DOCUMENTS

| WO | WO9919313 A1 | 4/1999 |
| WO | WO 0008002 A1 | 2/2000 |
| WO | WO 0023425 A1 | 4/2000 |
| WO | WO0023451 A1 | 4/2000 |
| WO | WO 0203415 A1 | 4/2000 |
| WO | WO 0063190 A1 | 10/2000 |
| WO | WO 0155085 A1 | 8/2001 |
| WO | WO 03011834 A1 | 2/2003 |

OTHER PUBLICATIONS

Wilson et al., The PPARs: From Orphan Receptors to Drug Discovery, Journal of Medicinal Chemistry, vol. 43, No. 4, pp. 527-550, Feb. 2000.*
Feb. 26, 2004 Search Report from corresponding International Application No. PCT/IB03/05371.

* cited by examiner

*Primary Examiner*—Brenda Coleman
(74) *Attorney, Agent, or Firm*—Buchanan Ingersoll & Rooney PC

(57) ABSTRACT

Disclosed is the preparation and pharmaceutical use of substituted arylalcanoic acid derivatives of Formula I, wherein ring A, ring B, $R^1$, $R^2$, $R^3$, $R^4$, $R^5$, X, $Alk^1$, $Alk^2$, $Ar^1$, and $Ar^2$ are as defined in the specification. These compounds, as selective agonists activating peroxisome proliferator-activated receptors (PPAR), in particularly the RXR/PPARalpha, RXR/PPARgamma, and RXR/PPARdelta heterodimers, are useful in the treatment and/or prevention of type 2 diabetes and associated metabolic syndrome such as hypertension, obesity, insulin resistance, hyperlipidemia, hyperglycemia, hypercholesterolemia, atherosclerosis, coronary artery disease, and other cardiovascular disorders with improved side effects profile commonly associated with conventional PPARgamma agonists.

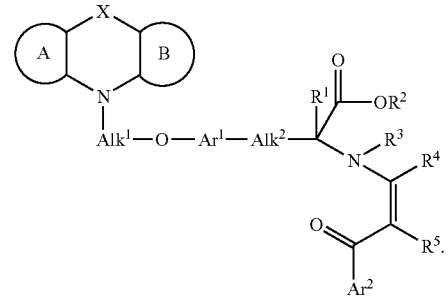

Formula I

15 Claims, 9 Drawing Sheets

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: PCR primer

```
<400> SEQUENCE: 1
acgtgcttcc tgcttcatag a                                          21

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
cctgagatta gccacctccc                                            20

<210> SEQ ID NO 3
<211> LENGTH: 41
<212> TYPE: DNA
<213> ORGANISM: Artificial Sequence
<220> FEATURE:
<223> OTHER INFORMATION: PPAR response element

<400> SEQUENCE: 3
gatcctctcc tttgacctat tgaactatta cctacatttg a                    41

<210> SEQ ID NO 4
<211> LENGTH: 28
<212> TYPE: DNA
<213> ORGANISM: Artificial Sequence
<220> FEATURE:
<223> OTHER INFORMATION: PCR primer

<400> SEQUENCE: 4
ggggtacctg cttcagcagc gtgttcga                                   28

<210> SEQ ID NO 5
<211> LENGTH: 28
<212> TYPE: DNA
<213> ORGANISM: Artificial Sequence
<220> FEATURE:
<223> OTHER INFORMATION: PCR primer

<400> SEQUENCE: 5
gctctagatg ttggcagtgg ctcaggac                                   28

<210> SEQ ID NO 6
<211> LENGTH: 45
<212> TYPE: DNA
<213> ORGANISM: Artificial Sequence
<220> FEATURE:
<223> OTHER INFORMATION: PPAR response element

<400> SEQUENCE: 6
cgcgttcctt tccgaacgtg accttttgtcc tggtcccctt ttgct               45
```

SUBSTITUTED ARYLALCANOIC ACID DERIVATIVES AS PPAR PAN AGONISTS WITH POTENT ANTIHYPERGLYCEMIC AND ANTIHYPERLIPIDEMIC ACTIVITY

Priority is indicated herein from U.S. Provisional Application Ser. No. 60/429,221, filed Nov. 26, 2002; and U.S. Provisional Application Ser. No. 60/469,368, filed May 9, 2003.

FIELD OF THE INVENTION

The present invention relates to the preparation and pharmaceutical use of novel substituted arylalcanoic acid derivatives. More particularly, the present invention relates to novel compounds of the general Formula (I), their preparation methods, their pharmaceutical compositions and their use for treatment and/or prevention of conditions mediated by nuclear receptors, in particular the RXR and PPAR heterodimers.

The present compounds are useful in treatment and/or prevention of type 2 diabetes and associated metabolic syndrome such as hypertension, obesity, insulin resistance, hyperlipidemia, hyperglycemia, hypercholesterolemia, atherosclerosis, coronary artery disease, and other cardiovascular disorders with improved side effects profile commonly associated with conventional PPARgamma agonists.

BACKGROUND OF THE INVENTION

Metabolic syndrome, including type 2 diabetes and associated complications such as obesity, cardiovascular symptoms, and dyslipidemia, are of major impact on social and economic significance. Although anti-diabetic treatments improve insulin resistance, they offer little protection from eminent cardiovascular risk associated with type 2 diabetes. Therefore, development of new treatments that have insulin sensitizing and cholesterol/triglycerides-lowering effects are of general interest.

Diabetes mellitus is a polygenic disorder affecting a significant portion of the people in the world. It is divided into two types. In type 1 diabetes, or insulin-dependent diabetes mellitus (IDDM), patients produce little or no insulin, the hormone that regulates glucose utilization. In type 2 diabetes, or noninsulin dependent diabetes mellitus (NIDDM), patients often have plasma insulin levels that are at the same compared to nondiabetic humans; however, these patients have developed a resistance to the insulin stimulating effect on glucose and lipid metabolism in the main insulin-sensitive tissues, i.e., muscle, liver and adipose tissues, and the plasma insulin levels are insufficient to overcome the pronounced insulin resistance. Type 2 diabetes consists of over 90% of all diabetes. It is a metabolic disorder characterized by hyperglycemia leading to secondary complications such as neuropathy, nephropathy, retinopathy, hypertriglyceridemia, obesity, and other cardiovascular diseases generally referred as metabolic syndrome.

The treatment generally prescribed for type 2 diabetes has been a combination of diet, exercise, and oral hypoglycemic agents, commonly sulfonylurea and biguanides. However, sulfonylurea therapy has many problems associated with primary and secondary failure of efficacy, incidence of hypoglycemia, and obesity. The biguanides therapy can induce lactic acidosis, nausea and diarrhea. Hence, a drug that can control plasma glucose tightly without significant side effects would be an important addition to diabetes therapy. Recently, a class of compounds termed thiazolidinediones has been shown to reduce hyperglycemia by promoting insulin action without additional insulin secretion, and without causing undesirable hypoglycemia, even at elevated doses. Their effect is proposed to be a result of initiation and modulation of adipocyte differentiation by agonist activity of PPARgamma. This class of compounds that is able to activate PPARgamma has been demonstrated clinically effective in treatment of type 2 diabetes (AVANDIA from GSK and ACTOS from Lilly/Tekada). Although the exact link from activation of PPARgamma to change in glucose metabolism, most notably a decrease in insulin resistance in muscle, have not yet been clarified. The link is via free fatty acids in such that activation of PPARgamma induces lipoprotein lipase, fatty acid transport protein and acyl-CoA synthetase in adipose tissue but not in muscle cells. This effect, in turn, reduces the concentration of free fatty acids in plasma dramatically, leading to eventual switch from fatty acid oxidation to glucose oxidation in high metabolic state of tissues, such as skeletal muscle and other tissues, due to substrate competition and pathway compensation. That results in a decreased insulin resistance in those tissues. Further, activation of PPARgamma modulates a subset of genes in controlling glucose and energy homeostasis, which leads to decrease blood glucose level (T. M. Wilson et al. "The PPARs: from orphan receptors to drug discovery" *J. Med. Chem.* 2000 43:527-50; A. Chawla et al. "Nuclear receptors and lipid physiology: Opening the X-files", *Science* 2001 294:1866-70).

Despite the advances made with the thiazolidinedione class of antidiabetes agents, serious unacceptable side effects including cardiac hypertrophy, hemodilution and liver toxicity have limited their clinical use. In the United States and Japan, several cases of liver damage and drug-related deaths due to liver damage have been reported. Further, PPARgamma-selective ligands induce adipocyte differentiation and white fat accumulation that leads to obesity, an important factor linking directly to the onset or the consequence of type 2 diabetes. Such unwanted effects will eventually compromise the insulin-sensitizing benefit of PPARgamma ligands. Hence, there is a definite need for a safe and efficacious agent for the treatment of type 2 diabetic patients that possesses dual activities of insulin-sensitizing as well as lowering white adipose deposition by regulating free fatty acids and triglycerides contents.

PPARgamma is a member of ligand-activated nuclear hormone receptor superfamily and expressed primarily in adipose tissues. A class of ligands named fibrates that are known to have triglyceride- and cholesterol-lowering activity activates another member of this family, the PPARalpha, which is mainly expressed in tissues such as liver. PPARalpha stimulates peroxisomal proliferation that enhances fatty acid oxidation, leading to reduced fatty acids level in blood (Keller and Wahli: *Trends Endocrin Metab* 1993, 4:291-296). Most recently, PPARdelta was reported to modulate lipid metabolism in which PPARdelta serves as a widespread regulator of fat burning. In vitro, activation of PPARdelta in adipocytes and skeletal muscle cells promotes fatty acid oxidation and utilization. Targeted activation of PPARdelta in adipose tissue in animals where PPARalpha is much less expressed, specifically induces expression of genes required for fatty acid oxidation and energy dissipation, which in turn leads to improved lipid profiles and reduced adiposity. Importantly, these animals are completely resistant to both high-fat diet-induced and genetically predisposed (Lepr(db/db)) obesity. Acute treatment of Lepr(db/db) mice with a PPARdelta agonist depletes lipid accumulation. In parallel, PPARdelta-deficient mice challenged with high-fat diet show reduced energy uncoupling and are prone to obesity (Wang Y X et al., Cell 2003 Apr. 18; 113(2):159-70). The transcriptional repression of atherogenic inflammation by ligand-activated PPARdelta was also reported, which further indicates the importance of PPARdelta in combating cardiovascular diseases (Lee, C H et al., Science 302:453-457, 2003).

PPARalpha, gamma, and delta form heterodimers with Retinoid X Receptor (RXR). The RXR/PPAR heterodimers thus play an essential role in controlling and regulating cellular events such as lipid, glucose homeostasis, and adipocyte differentiation. Several new chemical compounds were reported to have either PPARgamma activity or PPAR alpha and gamma dual activities that are beneficial in the treatment and/or prevention of metabolic syndromes in animal and in men (WO 00/08002, WO 01/57001 A1, U.S. Pat. No. 6,054,453, EP 088317 B1, WO97/25042, WO02/26729 A2, and U.S. Pat. No. 6,353,018 B1). The novel pan agonists that activate PPAR alpha, gamma, and delta should therefore be a very important addition to bring comprehensive management for metabolic syndrome X such as diabetes, hypertension, obesity, insulin resistance, hyperlipidemia, hyperglycemia, hypercholesterolemia, atherosclerosis, coronary artery disease, and other cardiovascular disorders.

SUMMARY OF THE INVENTION

One aspect of the present invention provides compounds of the Formula I:

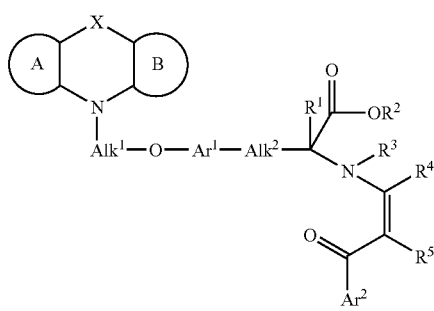

wherein
  ring A and ring B, fused to the ring containing X and N, independently of each other represents a 5-6 membered cyclic ring, which may optionally contain one or more heteroatoms selected from oxygen, sulfur or nitrogen atoms and optionally may be substituted with one or more halogen, hydroxy, nitro, cyano, alkyl, alkenyl, alkenynyl, aralkyl, heteroarylalkyl, aminoalkyl, alkoxyalkyl, aryloxyalkyl, aralkoxyalkyl, hydroxyalkyl, thioalkyl, heterocyclyl, alkoxy, aryl, aryloxy, aralkoxy, heteroaryl, heteroaryloxy, heteroaralkoxy, acyl, acyloxy, amino, alkylamino, arylamino, or aralkylamino; the ring A and ring B may be saturated or contain one or more double bonds or may be aromatic;
  X is a valence bond, $CH_2CH_2$, $CH=CH$, O, S, or $NR^6$ wherein $R^6$ represents H, alkyl, alkenyl, alkenynyl, aralkyl, heteroarylalkyl, heterocyclyl, aryl, or heteroaryl;
  $R^1$ is H, alkyl, alkenyl, alkenynyl, aralkyl, heteroarylalkyl, aminoalkyl, alkoxyalkyl, aryloxyalkyl, aralkoxyalkyl, hydroxyalkyl, thioalkyl, heterocyclyl, OH, halogen, alkoxy, aryl, aryloxy, aralkoxy, heteroaryl, heteroaryloxy, heteroaralkoxy, acyl, acyloxy, amino, alkylamino, arylamino, or aralkylamino;
  $R^2$ is H, alkyl, alkenyl, alkenynyl, aralkyl, heteroarylalkyl, heterocyclyl, aryl, or heteroaryl;
  $R^3$ is H, alkyl, alkenyl, alkenynyl, aralkyl, heteroarylalkyl, heterocyclyl, aryl, or heteroaryl;
  $R^4$ and $R^5$ are independently H, alkyl, alkenyl, alkenynyl, aralkyl, heteroarylalkyl, aminoalkyl, alkoxyalkyl, aryloxyalkyl, aralkoxyalkyl, hydroxyalkyl, thioalkyl, heterocyclyl, OH, halogen, alkoxy, aryl, aryloxy, aralkoxy, heteroaryl, heteroaryloxy, heteroaralkoxy, acyl, acyloxy, amino, alkylamino, arylamino, or aralkylamino; $R^4$ and $R^5$ may form a 5 or 6 membered ring optionally substituted with one or more halogen, hydroxy, nitro, cyano, alkyl, alkenyl, alkenynyl, aralkyl, heteroarylalkyl, aminoalkyl, alkoxyalkyl, aryloxyalkyl, aralkoxyalkyl, hydroxyalkyl, thioalkyl, heterocyclyl, alkoxy, aryl, aryloxy, aralkoxy, heteroaryl, heteroaryloxy, heteroaralkoxy, acyl, acyloxy, amino, alkylamino, arylamino, or aralkylamino;
  $Alk^1$ represents $C_{1-6}$alkylene;
  $Alk^2$ represents $C_{1-2}$alkylene;
  $Ar^1$ represents arylene, hetero arylene, or a divalent heterocyclic group optionally substituted with one or more halogen, $C_{1-6}$alkyl, amino, hydroxy, $C_{1-6}$alkoxyl or aryl.
  $Ar^2$ represents an aryl group substituted with none, one or more halogen, $C_{1-6}$-alkyl, amino, hydroxy, $C_{1-6}$alkoxyl or aryl; a hetero aryl, or a heterocyclic group optionally substituted with one or more halogen, $C_{1-6}$alkyl, amino, hydroxy, $C_{1-6}$alkoxyl or aryl.

Another aspect of the present invention relates to a pharmaceutical composition containing an active ingredient, at least one of the compounds of the general Formula (I), and/or a pharmaceutically acceptable salt thereof together with a pharmaceutically acceptable carrier or diluent for treatment and/or prevention of type 2 diabetes and associated metabolic syndrome such as hypertension, obesity, insulin resistance, hyperlipidemia, hyperglycemia, hypercholesterolemia, atherosclerosis, coronary artery disease, and other cardiovascular disorders.

It was unexpectedly discovered that the compounds of Formula I are able to decrease hyperglycemia and hypertriglyceremia associated with type 2 diabetes. It was also unexpectedly discovered that the compounds of Formula I can be used as pan agonists for RXR/PPARalpha, RXR/PPARgamma, and RXR/PPARdelta heterodimers, as well as agents for lowering both glucose and triglycerides levels for treatment and/or prevention of type 2 diabetes and associated metabolic syndrome.

The contents of the patents and publications cited herein and contents of documents cited in these patents and publications are hereby incorporated herein by reference to the extent permitted.

DETAILED DESCRIPTION OF THE INVENTION

Figure 1:
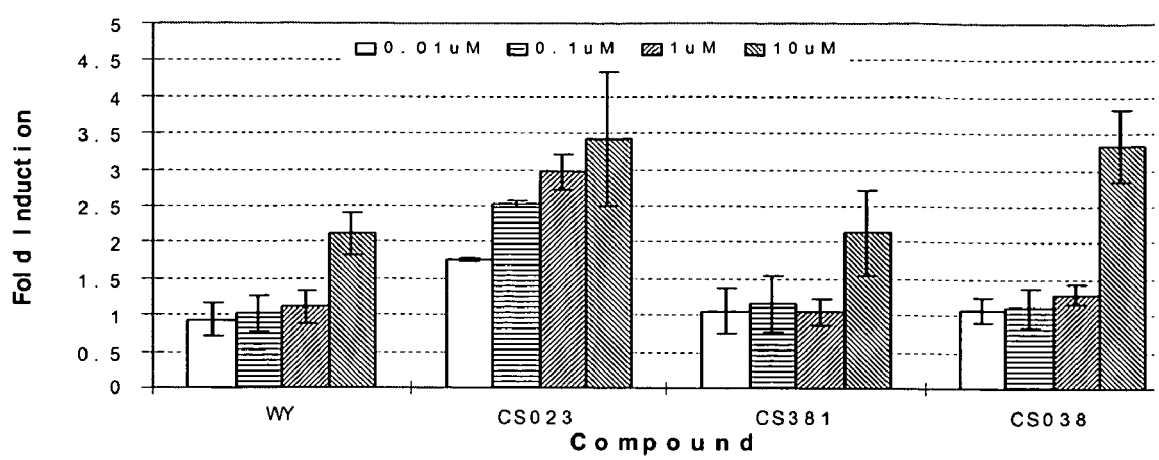
FIG. 1 graphically illustrates comparative activation of RXR/PPAR alpha heterodimers by compounds of the present invention (Example 30).

Unless defined otherwise, all technical and scientific terms used herein have the same meaning as is commonly understood by one of skill in the art to which this invention belongs. All publications and patents referred to herein are incorporated by reference.

In the preferred embodiment, the compounds of this invention are those of the Formula I, wherein
ring A is a 6 membered aromatic ring;
ring B is a 6 membered aromatic ring;
X is a valence bond, $CH_2CH_2$, CH=CH, O or S;
$R^1$ is H or alkyl;
$R^2$ is H or alkyl;
$R^3$ is H or alkyl;
$R^4$ and $R^5$ are independently H or alkyl;
$Alk^1$ is $C_{2-3}$alkylene;
$Alk^2$ is $C_{1-2}$alkylene;
$Ar^1$ is an arylene group
$Ar^2$ is a substituted aryl group.

In another preferred embodiment, the compounds of this invention are those of the Formula I, wherein
ring A is a 6 membered aromatic ring;
ring B is a 6 membered aromatic ring;
X is a valence bond, $CH_2CH_2$, CH=CH, O or S;
$R^1$ is H or alkyl;
$R^2$ is H or alkyl;
$R^3$ is H or alkyl;
$R^4$ and $R^5$ form a 6 membered aromatic ring;
$Alk^1$ is $C_{2-3}$alkylene;
$Alk^2$ is $C_{1-2}$alkylene;
$Ar^1$ is 6 membered aromatic ring
$Ar^2$ is a substituted aryl group.

In another preferred embodiment, the compounds of this invention are those of the Formula I, wherein
ring A is a benzene ring;
ring B is a benzene ring;
X is a valence bond, $CH_2CH_2$, CH=CH, O or S;
$R^1$ is H;
$R^2$ is H;
$R^3$ is H;
$R^4$ is methyl; $R^5$ is H;
$Alk^1$ is $CH_2CH_2$;
$Alk^2$ is $CH_2$;
$Ar^1$ is benzene ring;
$Ar^2$ is benzene ring substituted with none, one or more fluorine.

In a further preferred embodiment, the compounds of this invention are those of the Formula I, wherein
ring A is a benzene ring;
ring B is a benzene ring;
X is a valence bond, $CH_2CH_2$, CH=CH, O or S;
$R^1$ is H;
$R^2$ is H;
$R^3$ is H;
$R^4$ and $R^5$ form a benzene ring;
$Alk^1$ is $CH_2CH_2$;
$Alk^2$ is $CH_2$;
$Ar^1$ is benzene ring;
$Ar^2$ is benzene ring substituted with none, one or more fluorine.

In another preferred embodiment, the compounds of this invention are those of the Formula I, wherein
ring A is a benzene ring;
ring B is a benzene ring;
X is a valence bond, $CH_2CH_2$, CH=CH, O or S;
$R^1$ is H;
$R^2$ is H;
$R^3$ is H;
$R^4$ is methyl; $R^5$ is H;
$Alk^1$ is $CH_2CH_2$;
$Alk^2$ is $CH_2$;
$Ar^1$ is benzene ring;
$Ar^2$ is pyridine ring substituted with none, one or more halogen.

In a further preferred embodiment, the compounds of this invention are those of the Formula I, wherein
ring A is a benzene ring;
ring B is a benzene ring;
X is a valence bond, $CH_2CH_2$, CH=CH, O or S;
$R^1$ is H;
$R^2$ is H;
$R^3$ is H;
$R^4$ and $R^5$ form a benzene ring;
$Alk^1$ is $CH_2CH_2$;
$Alk^2$ is $CH_2$;
$Ar^1$ is benzene ring;
$Ar^2$ is pyridine ring substituted with none, one or more fluorine.

As used herein, the following terms have the indicated meaning:

The term "alkyl" as used herein is intended to include those alkyl groups in either a linear or branched or cyclic configuration. Typical alkyl groups include, but are not limited to, methyl, ethyl, n-propyl, iso-propyl, butyl, iso-butyl, sec-butyl, tert-butyl, penyl, iso-pentyl, hexyl, iso-hexyl, cyclopropyl, cyclobutyl, cyclopentyl, cyclohexyl and the like.

The term "aralkyl" as used herein refers to a straight or branched saturated carbon chain containing from 1 to 6 carbons substituted with an aromatic carbohydride, such as benzyl, phenethyl, 3-phenylpropyl, 1-naphtylmethyl and the like.

The term "heteroaralkyl" as used herein refers to a strait or branched saturated carbon chain containing from 1 to 6 carbons substituted with a heteroaryl as defined herein, such as (2-furyl)methyl, (3-furyl)methyl, (2-pyridyl)methyl and the like.

The term "aminoalkyl" as used herein refers to an alkyl as defined herein whereto is attached an amino group, such as aminoethyl, 1-aminopropyl, 2-aminopropyl and the like.

The term "alkoxyalkyl" as used herein refers to an alkyl as defined herein whereto is attached an alkoxy as defined herein, such as methoxymethyl, ethoxymethyl, methoxyethyl, ethoxyethyl and the like.

The term "aryloxyalkyl" as used herein refers to an alkyl as defined herein whereto is attached an aryloxy as defined herein, such as phenoxymethyl, phenoxydodecyl, 1-naphthyloxyethyl and the like.

The term "aralkoxyalkyl" as used herein refers to an alkyl as defined herein whereto is attached an aralkoxy as defined herein, such as benzyloxymethyl, 3-phenylpropoxyethyl and the like.

The term "hydroxyalkyl" as used herein refers to an alkyl as defined herein whereto is attached a hydroxy group, such as hydroxyethyl, 1-hydroxypropyl, 2-hydroxypropyl and the like.

The term "thioalkyl" as used herein refers to an alkyl as defined herein whereto is attached a group of Formula of —SR' wherein $R^1$ is H, alkyl or aryl, such as thiomethyl, methylthiomethyl, phenylthioethyl and the like.

The term "heterocyclyl" as used herein means a monovalent saturated or unsaturated group being monocyclic and containing one or more heteroatoms, such as pyrrolidine, pyrroline, pyrazoline, imidazolidine, imidazoline, piperidine, morpholine and the like.

The term "halogen" as used herein means fluorine, chlorine, bromine or iodine.

The term "alkoxy" as used herein is intended to include those alkyl groups in either a linear or branched or cyclic configuration linked through an ether oxygen having its free valence bond from the ether oxygen, such as methoxy, ethoxy, propoxy, butoxy, pentoxy, isopropoxy, sec-butoxy, cyclopropyloxy, cyclohexyloxy and the like.

The term "aryl" as used herein is intended to include aromatic rings optionally substituted with halogen, amino, hydroxy, alkyl or alkoxy, such as phenyl, naphthyl and the like.

The term "aryloxy" as used herein refers to phenoxy, 1-naphthyloxy, 2-naphthyloxy and the like.

The term "aralkoxy" as used herein refers to an alkyl as defined herein substituted with an aromatic carbohydride, such as benzyloxy, phenethoxy, 1-naphthylmethoxy and the like.

The term "heteroaryl" as used herein refers to a monovalent substituent comprising a 5-6 membered monocyclic aromatic system or a 9-10 membered bicyclic aromatic system containing one or more heteroatoms selected from nitrogen, oxygen and sulfur, such as furan, thiophene, pyrrole, imidazole, triazole, pyridine, pyrazine, pyrimidine, oxazole, quinoline, indole, benzimidazole and the like.

The term "heteroaryloxy" as used herein refers to a heteroaryl as defined herein linked to an oxygen atom having its free valence bond from the oxygen atom, such as pyrrole, imidazole, triazole, pyridine, pyrazine, pyrimidine, oxazole, quinoline, indole, benzimidazole linked to oxygen.

The term "heteroaralkoxy" as used herein refers to a heteroaralkyl as defined herein linked to an oxygen atom having its free valence bond from the oxygen atom, such as (2-furyl)methyl, (3-furyl)methyl, (2-pyridyl)methyl linked to oxygen.

The term "acyl" as used herein refers to a monovalent substituent comprising an alkyl group linked through a carbonyl group, such as acetyl, propionyl, butyryl, isobutyryl, pivaloyl, valeryl and the like.

The term "acyloxy" as used herein refers to an acyl as defined herein linked to an oxygen atom having its free valence bond from the oxygen atom, such as acetyloxy, propionyloxy, butyryloxy, isobutyryloxy, pivaloyloxy, valeryloxy and the like.

The term "alkylamino" as used herein refers to a straight or branched or cyclic monovalent substituent comprising an alkyl group linked through amino having a free valence bond from the nitrogen atom, such as methylamino, ethylamino, propylamino, butylamino, cyclopropylamino, cyclopentylamino, cyclohexylamino and the like.

The term "arylamino" as used herein refers to an aryl as defined herein linked through amino having a free valence bond from the nitrogen atom, such as phenylamino, naphthylamino and the like.

The term "aralkylamino" as used herein refers to an aralkyl as defined herein linked through amino having a free valence bond from the nitrogen atom, such as benzylamino, phenethylamino, 3-phenylpropylamino, 1-naphtylmethylamino and the like.

The compounds of Formula (I) can be prepared by the synthetic route shown in Scheme 1:

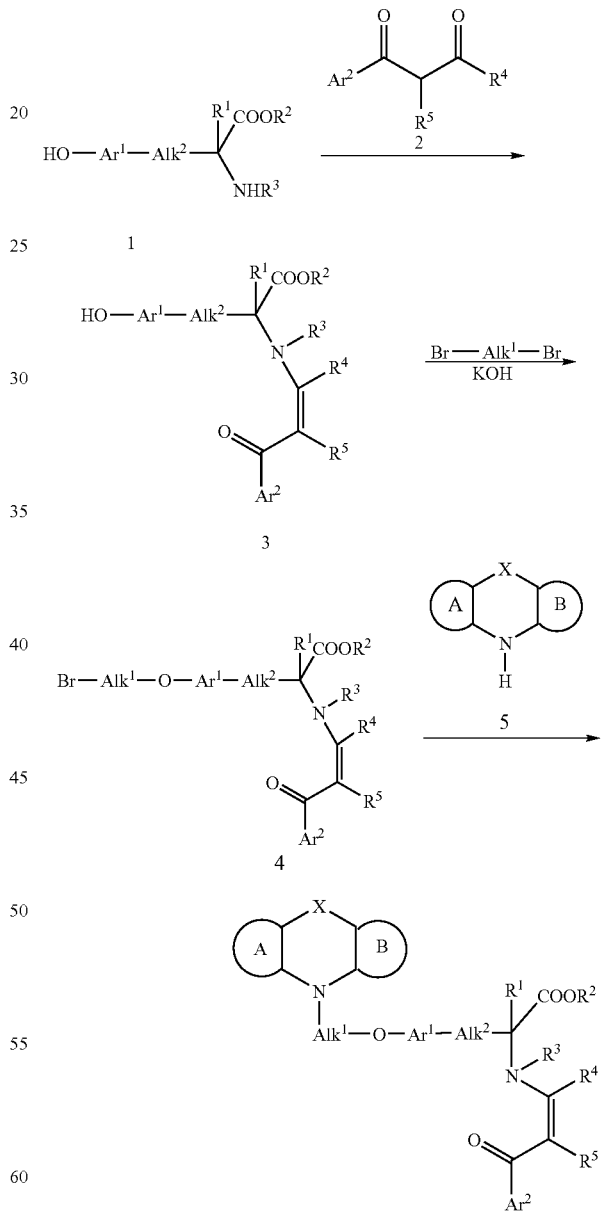

Compound 1 upon reaction with the β-diketone 2 gave the vinylogous amide analogues 3 in 95-98% yield. O-Alkylation of 3 in a routine manner by treatment with KOH and the corresponding dibromoalkane in ethanol gave the ether 4 in 15-20% yield. N-Alkylation of 4 by treatment with NaOH and compound 5 in the presence of tetrabutyl ammonium bromide gave the substituted arylalcanoic acid derivatives 6 in 20-25%.

The synthetic route shown in Scheme 1 is also suitable for the preparation of the compounds of Formula (I) where $Ar^2$ is benzene ring.

The pharmaceutical composition may be in the forms normally employed, such as tablets, capsules, powders, syrups, solutions, suspensions, aerosols, and the like, may contain flavourants, sweeteners etc. in suitable solids or liquid carriers or diluents, or in suitable sterile media to form injectable solutions or suspensions. In a preferred embodiment, the pharmaceutical composition contains up to about 65% of the compounds of Formula I by weight, preferably from about 0.5 to about 40%, more preferably from about 1 to about 20%, and most preferably from about 1 to 10% with the remainder of the composition being pharmaceutically acceptable carriers, diluents or solvents or salt solutions.

As used herein, the term "pharmaceutically acceptable carrier" or "diluent" includes, but is not limited to those disclosed in "Handbook of Pharmaceutical Excipients" published in October, 1986 by American Pharmaceutical Association, the content of which is incorporated herein by reference to the extent permitted.

The compounds of the Formula (I) as defined above are clinically administered to mammals, including man and animals, via oral, nasal, transdermal, pulmonary, or parenteral routes. Administration by the oral route is preferred, being more convenient and avoiding the possible pain and irritation of injection. In a preferred embodiment, the dosage is in the range from about 0.01 to about 200 mg/kg body weight per day administered singly or as a divided dose, preferably from about 0.01 to about 100 mg/kg and more preferably from about 0.1 to about 50 mg/kg. However, the optimal dosage for the individual subject being treated will be determined by the person responsible for treatment, generally a smaller dose being administered initially and thereafter increments made to determine the most suitable dosage.

Without intending to be bound by any particular theory of operation, it is believed that the administration of compounds of Formula I to patient treats diabetes and complications associated with it by lowering the patient's glucose and triglyceride levels. Such dual activities, for example, would help the patient to circumvent hyperglycemia and hypertriglyceremia associated with type 2 diabetes. It is also believed that treatment of type 2 diabetic patients and associated complications can be more effective and desirable if the glucose lowering and triglycerides lowering properties of treatment can be achieved by the treatment.

The following examples are given as specific illustrations of the invention. It should be understood, however, that the invention is not limited to the specific details set forth in the examples. All parts and percentages in the examples, as well as in the remainder of the specification, are by weight unless otherwise specified.

Further, any range of numbers recited in the specification or paragraphs hereinafter describing or claiming various aspects of the invention, such as that representing a particular set of properties, units of measure, conditions, physical states or percentages, is intended to literally incorporate expressly herein by reference or otherwise, any number falling within such range, including any subset of numbers or ranges subsumed within any range so recited. The term "about" when used as a modifier for, or in conjunction with, a variable, is intended to convey that the numbers and ranges disclosed herein are flexible and that practice of the present invention by those skilled in the art using temperatures, concentrations, amounts, contents, carbon numbers, and properties that are outside of the range or different from a single value, will achieve the desired result.

EXAMPLE 1

Preparation of 2-(1-methyl-3-oxo-3-phenyl-propenylamino)-3-(4-hydroxyphenyl)-propionic acid methyl ester

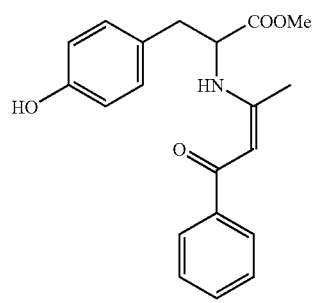

To a solution of L-tyrosine methyl ester (4.00 g, 20.51 mmol) in methanol (150 ml) is added 1-benzoylacetone (3.66 g, 22.56 mmol), then the mixture is heated to reflux for 24 h. The solvent is evaporated under a vacuum. To the residue is added ethanol (50 ml), then the ethanol is distilled off under atmospheric pressure. The crude product is purified by silica gel chromatography using hexane/EtOAc (4:1) as eluent to give the title compound (6.80 g, 98%).

EXAMPLE 2

Preparation of 2-(1-methyl-3-oxo-3-phenyl-propenylamino)-3-[4-(2-bromoethoxy)-phenyl]-propionic acid methyl ester

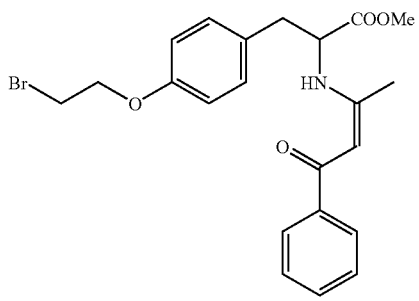

To a solution of potassium hydroxide (0.17 g, 2.95 mmol) in ethanol (20 ml) is added 2-(1-methyl-3-oxo-3-phenyl-propenylamino)-3-(4-hydroxyphenyl)-propionic acid methyl ester (1.00 g, 2.95 mmol) and 1,2-dibromoethane (5.54 g, 29.50 mmol). Then the mixture is heated to reflux for 8 hours. After cooled, the reaction mixture is filtered to remove the solid formed, and then the filtrate is evaporated under a vacuum. The crude product is purified by silica gel chromatography using hexane/EtOAc (4:1) as eluent to give the title compound (0.22 g, 17%).

EXAMPLE 3

Preparation of 2-(1-methyl-3-oxo-3-phenyl-propenylamino)-3-[4-(2-carbazolylethoxy)-phenyl]-propionic acid (compound CS023)

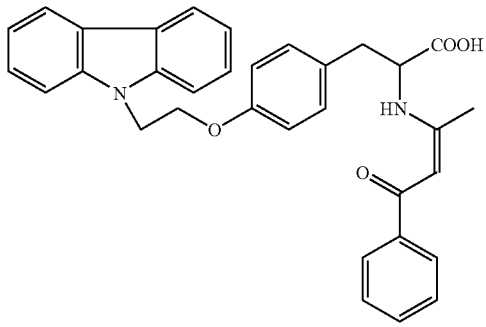

To a solution of 2-(1-methyl-3-oxo-3-phenyl-propenylamino)-3-[4-(2-bromoethoxy)-phenyl]-propionic acid methyl ester (0.22 g, 0.49 mmol) and carbazole (0.082 g, 0.49 mmol) in benzene (10 ml) is added tetrabutyl ammonium bromide (0.08 g) and 50% NaOH aqueous solution (0.084 g, 1.08 mmol), then the mixture is heated to reflux for 10 h. After cooled, benzene (30 ml) is added, and the mixture is washed with water(3×30 ml). Then the solvent is evaporated under a vacuum. The crude product is purified by silica gel chromatography using $CHCl_3$/MeOH (4:1) as eluent to give the title compound (0.05 g, 20%). HRMS calcd for $C_{33}H_{30}N_2O_4$: 518.6123. Found: 518.6125. MA calcd for $C_{33}H_{30}N_2O_4$: C, 76.43%; H, 5.83%; N, 5.40%. Found: C, 76.21%; H, 5.85%; N, 5.39%.

EXAMPLE 4

Preparation of 2-[1-methyl-3-oxo-3-(4-fluorophenyl)-propenylamino]-3-(4-hydroxyphenyl)-propionic acid methyl ester

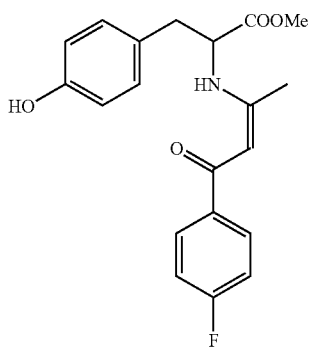

To a solution of L-tyrosine methyl ester (4.00 g, 20.51 mmol) in methanol (150 ml) is added 1-(4-fluorobenzoyl) acetone (4.06 g, 22.56 mmol), then the mixture is heated to reflux for 24 h. The solvent is evaporated under a vacuum. To the residue is added ethanol (50 ml), then the ethanol is distilled off under atmospheric pressure. The crude product is purified by silica gel chromatography using hexane/EtOAc (4:1) as eluent to give the title compound (7.03 g, 96%).

EXAMPLE 5

Preparation of 2-[1-methyl-3-oxo-3-(4-fluorophenyl)-propenylamino]-3-[4-(2-bromoethoxy)-phenyl]-propionic acid methyl ester

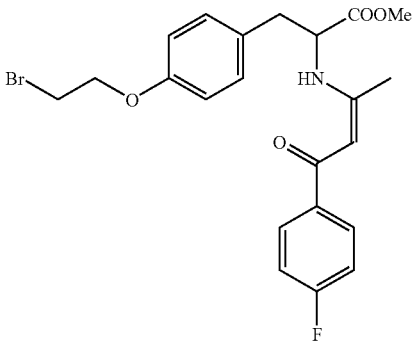

To a solution of potassium hydroxide (0.17 g, 2.95 mmol) in ethanol (20 ml) is added 2-[1-methyl-3-oxo-3-(4-fluorophenyl)-propenylamino]-3-(4-hydroxyphenyl)-propionic acid methyl ester (1.05 g, 2.95 mmol) and 1,2-dibromoethane (5.54 g, 29.50 mmol). Then the mixture is heated to reflux for 8 hours. After cooled, the reaction mixture is filtered to remove the solid formed, and then the filtrate is evaporated under a vacuum. The crude product is purified by silica gel chromatography using hexane/EtOAc (4:1) as eluent to give the title compound (0.37 g, 27%).

EXAMPLE 6

Preparation of 2-[1-methyl-3-oxo-3-(4-fluorophenyl)-propenylamino]-3-[4-(2-carbazolylethoxy)-phenyl]-propionic acid

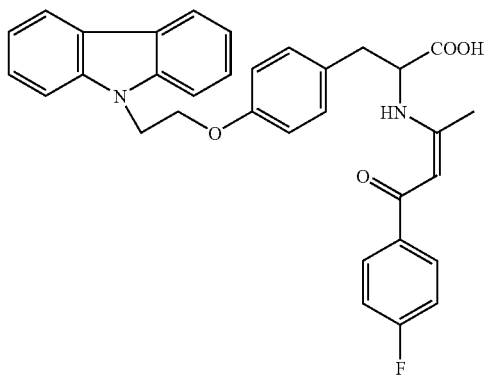

To a solution of 2-[1-methyl-3-oxo-3-(4-fluorophenyl)-propenylamino]-3-[4-(2-bromoethoxy)-phenyl]-propionic acid methyl ester (0.23 g, 0.49 mmol) and carbazole (0.082 g, 0.49 mmol) in benzene (10 ml) is added tetrabutyl ammonium bromide (0.08 g) and 50% NaOH aqueous solution (0.084 g, 1.08 mmol), then the mixture is heated to reflux for 10 h. After cooled, benzene (30 ml) is added, and the mixture is washed with water(3×30 ml). Then the solvent is evaporated under a vacuum. The crude product is purified by silica gel chromatography using CHCl$_3$/MeOH (4:1) as eluent to give the title compound (0.06 g, 23%). HRMS calcd for C$_{33}$H$_{29}$FN$_2$O$_4$: 536.6027. Found: 536.6025. MA calcd for C$_{33}$H$_{29}$FN$_2$O$_4$: C, 73.86%; H, 5.45%; N, 5.22%. Found: C, 73.63%; H, 5.46%; N, 5.20%.

EXAMPLE 7

Preparation of 2-[1-methyl-3-oxo-3-(3-pyridyl)-propenylamino]-3-(4-hydroxyphenyl)-propionic acid methyl ester

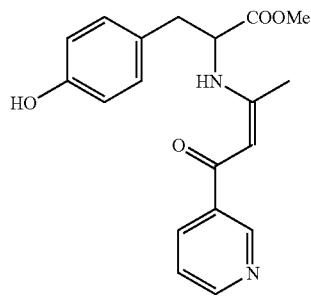

To a solution of L-tyrosine methyl ester (4.00 g, 20.51 mmol) in methanol (150 ml) is added 1-nicotinoylacetone (3.68 g, 22.56 mmol), then the mixture is heated to reflux for 24 h. The solvent is evaporated under a vacuum. To the residue is added ethanol (50 ml), then the ethanol is distilled off under atmospheric pressure. The crude product is purified by silica gel chromatography using hexane/EtOAc (4:1) as eluent to give the title compound (5.51 g, 79%).

EXAMPLE 8

Preparation of 2-[1-methyl-3-oxo-3-(3-pyridyl)-propenylamino]-3-[4-(2-bromoethoxy)-phenyl]-propionic acid methyl ester

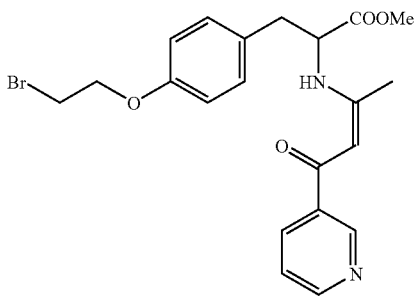

To a solution of potassium hydroxide (0.17 g, 2.95 mmol) in ethanol (20 ml) is added 2-[1-methyl-3-oxo-3-(3-pyridyl)-propenylamino]-3-(4-hydroxyphenyl)-propionic acid methyl ester (1.00 g, 2.95 mmol) and 1,2-dibromoethane (5.54 g, 29.50 mmol). Then the mixture is heated to reflux for 8 hours. After cooled, the reaction mixture is filtered to remove the solid formed, and then the filtrate is evaporated under a vacuum. The crude product is purified by silica gel chromatography using hexane/EtOAc (4:1) as eluent to give the title compound (0.20 g, 15%).

EXAMPLE 9

Preparation of 2-[1-methyl-3-oxo-3-(3-pyridyl)-propenylamino]-3-[4-(2-carbazolylethoxy)-phenyl]-propionic acid

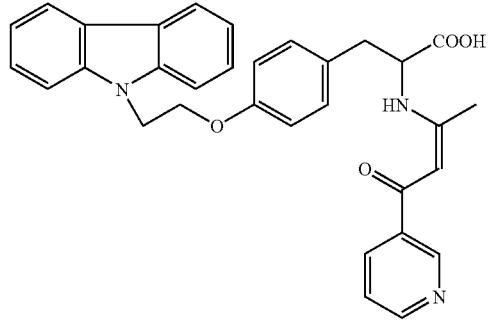

To a solution of 2-(1-methyl-3-oxo-3-(3-pyridyl)-propenylamino)-3-[4-(2-bromoethoxy)-phenyl]-propionic acid methyl ester (0.22 g, 0.49 mmol) and carbazole (0.082 g, 0.49 mmol) in benzene (10 ml) is added tetrabutyl ammonium bromide (0.08 g) and 50% NaOH aqueous solution (0.084 g, 1.08 mmol), then the mixture is heated to reflux for 10 h. After cooled, benzene (30 ml) is added, and the mixture is washed with water(3×30 ml). Then the solvent is evaporated under a vacuum. The crude product is purified by silica gel chromatography using CHCl$_3$/MeOH (4:1) as eluent to give the title compound (0.04 g, 16%). HRMS calcd for C$_{32}$H$_{29}$N$_3$O$_4$: 519.6001. Found: 519.6003. MA calcd for C$_{32}$H$_{29}$N$_3$O$_4$: C, 73.97%; H, 5.63%; N, 8.09%. Found: C, 73.84%; H, 5.65%; N, 8.11%.

EXAMPLE 10

Preparation of 2-((2-benzoylphenyl)amino)-3-(4-hydroxyphenyl)-propionic acid methyl ester

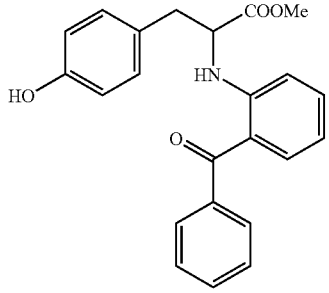

To a mixture of 2-benzoylcyclohexanone (90.9 g, 0.45 mol), L-tyrosine methyl ester (78.0 g, 0.40 mol) in anisole (1000 ml) is added 5% palladium on carbon (20 g), then the mixture is heated to reflux for 2 h while the resulting water is removed by a Dean-Stark apparatus. The mixture is cooled to 80° C., and the Pd/C is filtered and washed with anisole (3×60 ml). The mixture is cooled to 40° C., hexane (1000 ml) is added and the mixture kept at −20° C. for 48 h. The solid is filtered and washed with hexane (5×200 ml) to yield the crude 2-((2-benzoylphenyl)-amino)-3-(4-hydroxyphenyl)-propionic acid methyl ester. The crude product is mixed with 250 ml of methanol and is refluxed for 30 min. After cooled to 0° C., the product is filtered, washed with methanol (2×50 ml), and dried under a vacuum to give the title compound (60.2 g, 40.1%).

EXAMPLE 11

Preparation of 2-((2-benzoylphenyl)amino)-3-[4-(2-bromoethoxy)-phenyl]-propionic acid methyl ester

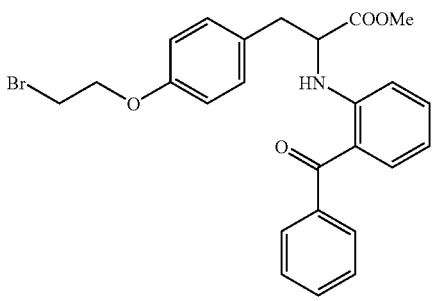

To a solution of potassium hydroxide (0.17 g, 2.95 mmol) in ethanol (20 ml) is added 2-((2-benzoylphenyl)amino)-3-(4-hydroxyphenyl)-propionic acid methyl ester (1.11 g, 2.95 mmol) and 1,2-dibromoethane (5.54 g, 29.50 mmol). Then the mixture is heated to reflux for 8 hours. After cooled, the reaction mixture is filtered to remove the solid formed, and then the filtrate is evaporated under a vacuum. The crude product is purified by silica gel chromatography using hexane/EtOAc (4:1) as eluent to give the title compound (0.30 g, 21%).

EXAMPLE 12

Preparation of 2-((2-benzoylphenyl)amino)-3-[4-(2-carbazolylethoxy)-phenyl]-propionic acid (compound CS0381)

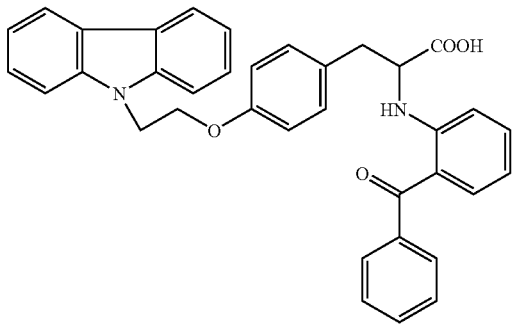

To a solution of 2-((2-benzoylphenyl)amino)-3-[4-(2-bromoethoxy)-phenyl]-propionic acid methyl ester (0.24 g, 0.49 mmol) and carbazole (0.082 g, 0.49 mmol) in benzene (10 ml) is added tetrabutyl ammonium bromide (0.08 g) and 50% NaOH aqueous solution (0.084 g, 1.08 mmol), then the mixture is heated to reflux for 10 h. After cooled, benzene (30 ml) is added, and the mixture is washed with water(3×30 ml). Then the solvent is evaporated under a vacuum. The crude product is purified by silica gel chromatography using CHCl$_3$/MeOH (4:1) as eluent to give the title compound (0.06 g, 22%). HRMS calcd for C$_{36}$H$_{30}$N$_2$O$_4$: 554.6453. Found: 554.6451. MA calcd for C$_{36}$H$_{30}$N$_2$O$_4$: C, 77.96%; H, 5.45%; N, 5.05%. Found: C, 77.83%; H, 5.46%; N, 5.07%.

EXAMPLE 13

Preparation of 2-[(2-(4-fluorobenzoyl)phenyl)amino]-3-(4-hydroxyphenyl)-propionic acid methyl ester

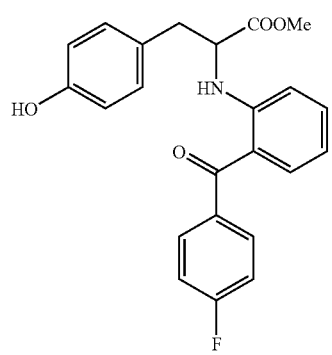

To a mixture of 2-(4-fluorobenzoyl)cyclohexanone (99.0 g, 0.45 mol), L-tyrosine methyl ester (78.0 g, 0.40 mol) in anisole (1000 ml) is added 5% palladium on carbon (20 g), then the mixture is heated to reflux for 2 h while the resulting water is removed by a Dean-Stark apparatus. The mixture is cooled to 80° C., and the Pd/C is filtered and washed with anisole (3×60 ml). The mixture is cooled to 40° C., hexane (1000 ml) is added and the mixture kept at −20° C. for 48 h. The solid is filtered and washed with hexane (5×200 ml) to yield the crude 2-[(2-(4-fluorobenzoyl)phenyl)amino]-3-(4-hydroxyphenyl)-propionic acid methyl ester. The crude product is mixed with 250 ml of methanol and is refluxed for 30 min. After cooled to 0° C., the product is filtered, washed with methanol (2×50 ml), and dried under a vacuum to give the title compound (75.6 g, 48.1%).

EXAMPLE 14

Preparation of 2-[(2-(4-fluorobenzoyl)phenyl)amino]-3-[4-(2-bromoethoxy)-phenyl]-propionic acid methyl ester

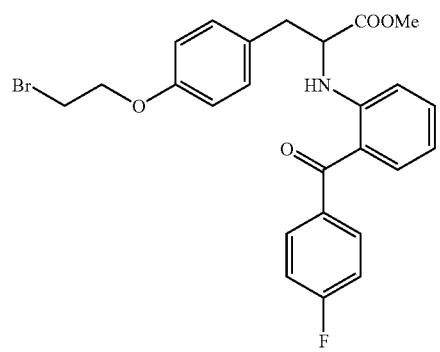

To a solution of potassium hydroxide (0.17 g, 2.95 mmol) in ethanol (20 ml) is added 2-[(2-(4-fluorobenzoyl)phenyl) amino]-3-(4-hydroxyphenyl)-propionic acid methyl ester (1.16 g, 2.95 mmol) and 1,2-dibromoethane (5.54 g, 29.50 mmol). Then the mixture is heated to reflux for 8 hours. After cooled, the reaction mixture is filtered to remove the solid formed, and then the filtrate is evaporated under a vacuum. The crude product is purified by silica gel chromatography using hexane/EtOAc (4:1) as eluent to give the title compound (0.56 g, 38%).

EXAMPLE 15

Preparation of 2-[(2-(4-fluorobenzoyl)phenyl)amino]-3-[4-(2-carbazolylethoxy)-phenyl]-propionic acid (compound CS038)

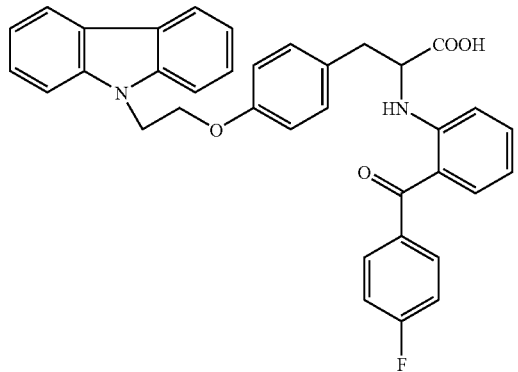

To a solution of 2-[(2-(4-fluorobenzoyl)phenyl)amino]-3-[4-(2-bromoethoxy)-phenyl]-propionic acid methyl ester (0.25 g, 0.49 mmol) and carbazole (0.082 g, 0.49 mmol) in benzene (10 ml) is added tetrabutyl ammonium bromide (0.08 g) and 50% NaOH aqueous solution (0.084 g, 1.08 mmol), then the mixture is heated to reflux for 10 h. After cooled, benzene (30 ml) is added, and the mixture is washed with water (3×30 ml). Then the solvent is evaporated under a vacuum. The crude product is purified by silica gel chromatography using CHCl$_3$/MeOH (4:1) as eluent to give the title compound (0.10 g, 36%). HRMS calcd for $C_{36}H_{29}FN_2O_4$: 572.6357. Found: 572.6354. MA calcd for $C_{36}H_{29}FN_2O_4$: C, 75.51%; H, 5.11%; N, 4.89%. Found: C, 75.83%; H, 5.10%; N, 4.90%.

EXAMPLE 16

Preparation of 2-((2-nicotinoylphenyl)amino)-3-(4-hydroxyphenyl)-propionic acid methyl ester

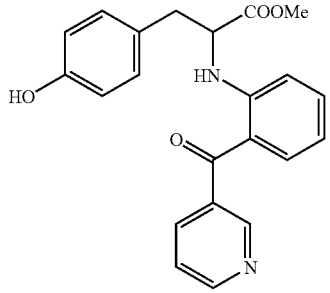

To a mixture of 2-nicotinoylcyclohexanone (914.0 g, 0.45 mol), L-tyrosine methyl ester (78.0 g, 0.40 mol) in anisole (1000 ml) is added 5% palladium on carbon (20 g), then the mixture is heated to reflux for 2 h while the resulting water is removed by a Dean-Stark apparatus. The mixture is cooled to 80° C., and the Pd/C is filtered and washed with anisole (3×60 ml). The mixture is cooled to 40° C., hexane (1000 ml) is added and the mixture kept at −20° C. for 48 h. The solid is filtered and washed with hexane (5×200 ml) to yield the crude 2-((2-nicotinoylphenyl)amino)-3-(4-hydroxyphenyl)-propionic acid methyl ester. The crude product is mixed with 250 ml of methanol and is refluxed for 30 min. After cooled to 0° C., the product is filtered, washed with methanol (2×50 ml), and dried under a vacuum to give the title compound (58.6 g, 39.0%).

EXAMPLE 17

Preparation of 2-((2-nicotinoylphenyl)amino)-3-[4-(2-bromoethoxy)-phenyl]-propionic acid methyl ester

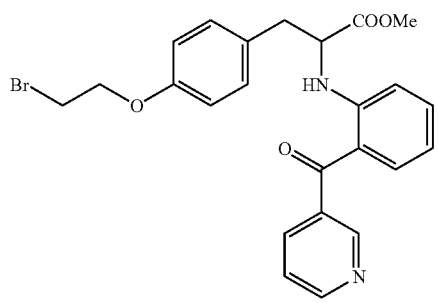

To a solution of potassium hydroxide (0.17 g, 2.95 mmol) in ethanol (20 ml) is added 2-((2-nicotinoylphenyl)amino)-3-(4-hydroxyphenyl)-propionic acid methyl ester (1.10 g, 2.95 mmol) and 1,2-dibromoethane (5.54 g, 29.50 mmol). Then the mixture is heated to reflux for 8 hours. After cooled, the reaction mixture is filtered to remove the solid formed, and then the filtrate is evaporated under a vacuum. The crude product is purified by silica gel chromatography using hexane/EtOAc (4:1) as eluent to give the title compound (0.40 g, 28.2%).

EXAMPLE 18

Preparation of 2-((2-nicotinoylphenyl)amino)-3-[4-(2-carbazolylethoxy)-phenyl]-propionic acid

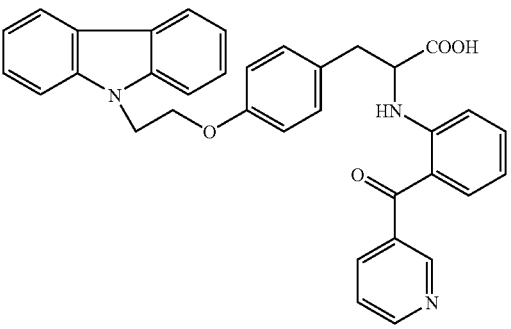

To a solution of 2-((2-nicotinoylphenyl)amino)-3-[4-(2-bromoethoxy)-phenyl]-propionic acid methyl ester (0.24 g, 0.49 mmol) and carbazole (0.082 g, 0.49 mmol) in benzene (10 ml) is added tetrabutyl ammonium bromide (0.08 g) and 50% NaOH aqueous solution (0.084 g, 1.08 mmol), then the mixture is heated to reflux for 10 h. After cooled, benzene (30 ml) is added, and the mixture is washed with water (3×30 ml). Then the solvent is evaporated under a vacuum. The crude product is purified by silica gel chromatography using CHCl$_3$/MeOH (4:1) as eluent to give the title compound (0.05 g, 18%). HRMS calcd for $C_{35}H_{29}N_3O_4$: 555.6331. Found: 555.6329. MA calcd for $C_{35}H_{29}N_3O_4$: C, 75.66%; H, 5.26%; N, 7.56%. Found: C, 75.42%; H, 5.27%; N, 7.53%.

EXAMPLE 19

The preparation process for scale up of 2-((2-benzoylphenyl)amino)-3-[4-(2-carbazolylethoxy)-phenyl]-propionic acid

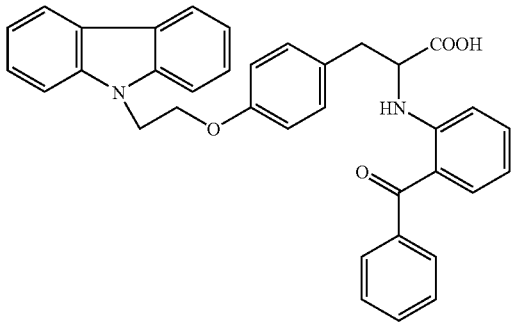

To a solution of potassium carbonate (2 kg) in acetonitrile (5000 ml) is added 2-((2-benzoylphenyl)amino)-3-(4-hydroxyphenyl)-propionic acid methyl ester (555 g, 1.48 mol) and 1,2-dibromoethane (1000 ml). Then the mixture is stirred at room temperature for 24 hours. After that, the reaction mixture is filtered, and then the filtrate is evaporated under a vacuum. The crude product is purified by silica gel chromatography using hexane/EtOAc (4:1) as eluent to give 2-((2-benzoylphenyl)amino)-3-[4-(2-bromoethoxy)-phenyl]-propionic acid methyl ester (442 g, 62%).

To a solution of 2-((2-benzoylphenyl)amino)-3-[4-(2-bromoethoxy)-phenyl]-propionic acid methyl ester (240 g, 0.49 mol) and carbazole (82 g, 0.49 mol) in benzene (3000 ml) is added tetrabutyl ammonium bromide (80 g) and 40% NaOH aqueous solution (105 g, 1.05 mol), then the mixture is heated to reflux for 10 h. After cooled, the upper organic layer is evaporated under a vacuum. The crude product is purified by silica gel chromatography using $CHCl_3$/MeOH (8:1) as eluent to give the title compound (78 g, 28.7%).

EXAMPLE 20

The preparation process for scale up of 2-[(2-(4-fluorobenzoyl)phenyl)amino]-3-[4-(2-carbazolylethoxy)-phenyl]-propionic acid

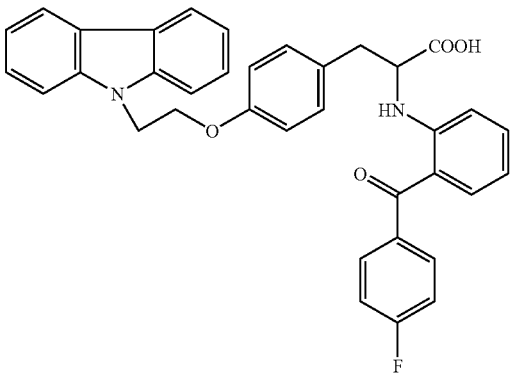

To a solution of potassium carbonate (2 kg) in acetonitrile (5000 ml) is added 2-[(2-(4-fluorobenzoyl)phenyl)amino]-3-(4-hydroxyphenyl)-propionic acid methyl ester (581 g, 1.48 mol) and 1,2-dibromoethane (1000 ml). Then the mixture is stirred at room temperature for 24 hours. After that, the reaction mixture is filtered, and then the filtrate is evaporated under a vacuum. The crude product is purified by silica gel chromatography using hexane/EtOAc (4:1) as eluent to give 2-[(2-(4-fluorobenzoyl)phenyl)amino]-3-[4-(2-bromoethoxy)-phenyl]-propionic acid methyl ester (429 g, 58%).

To a solution of 2-[(2-(4-fluorobenzoyl)phenyl)amino]-3-[4-(2-bromoethoxy)-phenyl]-propionic acid methyl ester (250 g, 0.50 mol) and carbazole (83.5 g, 0.50 mmol) in benzene (3000 ml) is added tetrabutyl ammonium bromide (80 g) and 40% NaOH aqueous solution (108 g, 1.08 mol), then the mixture is heated to reflux for 10 h. After cooled, the upper organic layer is evaporated under a vacuum. The crude product is purified by silica gel chromatography using $CHCl_3$/MeOH (8:1) as eluent to give the title compound (91.52 g, 32%).

EXAMPLE 21

Preparation of 2-[(2-(4-tert-butylbenzoyl)phenyl)amino]-3-(4-hydroxyphenyl)-propionic acid methyl ester

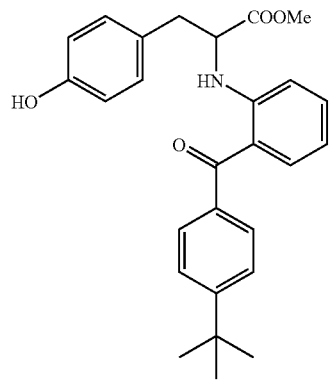

To a mixture of 2-(4-tert-butylbenzoyl)cyclohexanone (116.1 g, 0.45 mol), L-tyrosine methyl ester (78.0 g, 0.40 mol) in anisole (1000 ml) is added 5% palladium on carbon (20 g), then the mixture is heated to reflux for 2 h while the resulting water is removed by a Dean-Stark apparatus. The mixture is cooled to 80° C., and the Pd/C is filtered and washed with anisole (3×60 ml). The mixture is cooled to 40° C., hexane (1000 ml) is added and the mixture kept at −20° C. for 48 h. The solid is filtered and washed with hexane (5×200 ml) to yield the crude 2-[(2-(4-tert-butylbenzoyl) phenyl)-amino]-3-(4-hydroxyphenyl)-propionic acid methyl ester. The crude product is mixed with 250 ml of methanol and is refluxed for 30 min. After cooled to 0° C., the product is filtered, washed with methanol (2×50 ml), and dried under a vacuum to give the title compound (70.7 g, 41.0%).

EXAMPLE 22

Preparation of 2-[(2-(4-tert-butylbenzoyl)phenyl)amino]-3-[4-(2-bromoethoxy)-phenyl]-propionic acid methyl ester

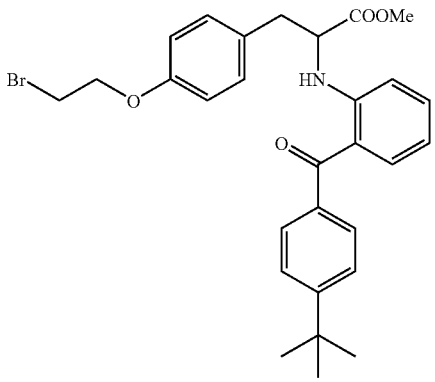

To a solution of potassium hydroxide (0.17 g, 2.95 mmol) in ethanol (20 ml) is added 2-[(2-(4-tert-butylbenzoyl)phenyl)amino]-3-(4-hydroxyphenyl)-propionic acid methyl ester (1.27 g, 2.95 mmol) and 1,2-dibromoethane (5.54 g, 29.50 mmol). Then the mixture is heated to reflux for 8 hours. After cooled, the reaction mixture is filtered to remove the solid formed, and then the filtrate is evaporated under a vacuum. The crude product is purified by silica gel chromatography using hexane/EtOAc (4:1) as eluent to give the title compound (0.67 g, 42%).

EXAMPLE 23

Preparation of 2-[(2-(4-tert-butylbenzoyl)phenyl)amino]-3-[4-(2-carbazolylethoxy)-phenyl]-propionic acid (Lab code CS0130090)

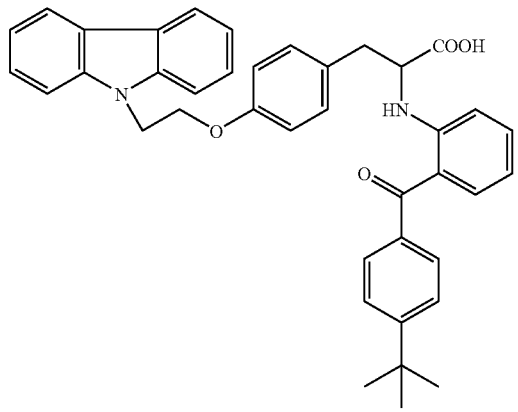

To a solution of 2-[(2-(4-tert-butylbenzoyl)phenyl)amino]-3-[4-(2-bromoethoxy)-phenyl]-propionic acid methyl ester (0.26 g, 0.49 mmol) and carbazole (0.082 g, 0.49 mmol) in benzene (10 ml) is added tetrabutyl ammonium bromide (0.08 g) and 50% NaOH aqueous solution (0.084 g, 1.08 mmol), then the mixture is heated to reflux for 10 h. After cooled, benzene (30 ml) is added, and the mixture is washed with water (3×30 ml). Then the solvent is evaporated under a vacuum. The crude product is purified by silica gel chromatography using $CHCl_3$/MeOH (4:1) as eluent to give the title compound (0.14 g, 47%). HRMS calcd for $C_{40}H_{38}N_2O_4$: 610.7496. Found: 610.7493. MA calcd for $C_{40}H_{38}N_2O_4$: C, 78.66%; H, 6.27%; N, 4.59%. Found: C, 78.85%; H, 6.24%; N, 4.61%.

EXAMPLE 24

Preparation of 2-[(2-(4-methylbenzoyl)phenyl)amino]-3-(4-hydroxyphenyl)-propionic acid methyl ester

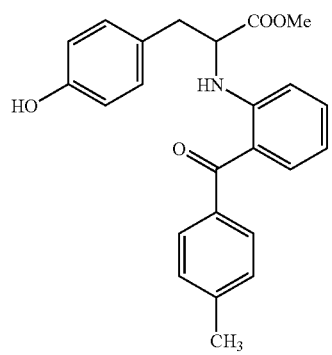

To a mixture of 2-(4-methylbenzoyl)cyclohexanone (97.2 g, 0.45 mol), L-tyrosine methyl ester (78.0 g, 0.40 mol) in anisole (1000 ml) is added 5% palladium on carbon (20 g), then the mixture is heated to reflux for 2 h while the resulting water is removed by a Dean-Stark apparatus. The mixture is cooled to 80° C., and the Pd/C is filtered and washed with anisole (3×60 ml). The mixture is cooled to 40° C., hexane (1000 ml) is added and the mixture kept at −20° C. for 48 h. The solid is filtered and washed with hexane (5×200 ml) to yield the crude 2-[(2-(4-methyl benzoyl)phenyl)-amino]-3-(4-hydroxyphenyl)-propionic acid methyl ester. The crude product is mixed with 250 ml of methanol and is refluxed for 30 min. After cooled to 0° C., the product is filtered, washed with methanol (2×50 ml), and dried under a vacuum to give the title compound (59.1 g, 38%).

EXAMPLE 25

Preparation of 2-[(2-(4-methylbenzoyl)phenyl)amino]-3-[4-(2-bromoethoxy)-phenyl]-propionic acid methyl ester

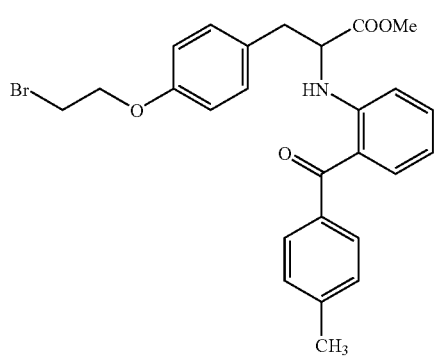

To a solution of potassium hydroxide (0.17 g, 2.95 mmol) in ethanol (20 ml) is added 2-[(2-(4-methylbenzoyl)phenyl)amino]-3-(4-hydroxyphenyl)-propionic acid methyl ester (1.15 g, 2.95 mmol) and 1,2-dibromoethane (5.54 g, 29.50 mmol). Then the mixture is heated to reflux for 8 hours.

After cooled, the reaction mixture is filtered to remove the solid formed, and then the filtrate is evaporated under a vacuum. The crude product is purified by silica gel chromatography using hexane/EtOAc (4:1) as eluent to give the title compound (0.78 g, 53%).

EXAMPLE 26

Preparation of 2-[(2-(4-methylbenzoyl)phenyl)amino]-3-[4-(2-carbazolylethoxy)-phenyl]-propionic acid (Lab code CS0130080)

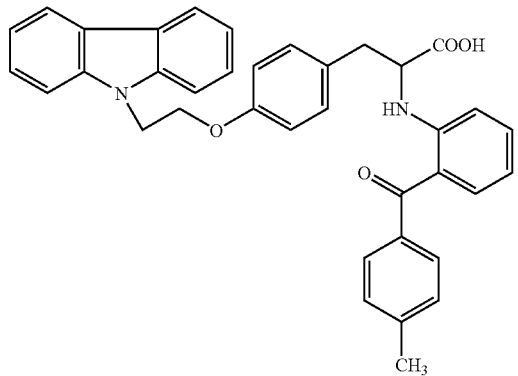

To a solution of 2-[(2-(4-methylbenzoyl)phenyl)amino]-3-[4-(2-bromoethoxy)-phenyl]-propionic acid methyl ester (0.24 g, 0.49 mmol) and carbazole (0.082 g, 0.49 mmol) in benzene (10 ml) is added tetrabutyl ammonium bromide (0.08 g) and 50% NaOH aqueous solution (0.084 g, 1.08 mmol), then the mixture is heated to reflux for 10 h. After cooled, benzene (30 ml) is added, and the mixture is washed with water (3×30 ml). Then the solvent is evaporated under a vacuum. The crude product is purified by silica gel chromatography using CHCl$_3$/MeOH (4:1) as eluent to give the title compound (0.15 g, 54%). HRMS calcd for C$_{37}$H$_{32}$N$_2$O$_4$: 568.6692. Found: 568.6693. MA calcd for C$_{37}$H$_{32}$N$_2$O$_4$: C, 78.15%; H, 5.67%; N, 4.93%. Found: C, 78.36%; H, 5.64%; N, 4.91%.

EXAMPLE 27

Preparation of 2-[(2-(2-methylbenzoyl)phenyl)amino]-3-(4-hydroxyphenyl)-propionic acid methyl ester

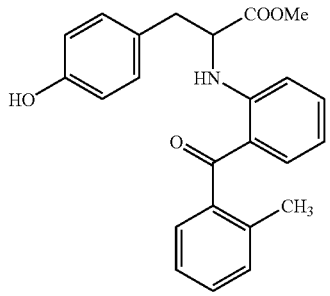

To a mixture of 2-(2-methylbenzoyl)cyclohexanone (97.2 g, 0.45 mol), L-tyrosine methyl ester (78.0 g, 0.40 mol) in anisole (1000 ml) is added 5% palladium on carbon (20 g), then the mixture is heated to reflux for 2 h while the resulting water is removed by a Dean-Stark apparatus. The mixture is cooled to 80° C., and the Pd/C is filtered and washed with anisole (3×60 ml). The mixture is cooled to 40° C., hexane (1000 ml) is added and the mixture kept at −20° C. for 48 h. The solid is filtered and washed with hexane (5×200 ml) to yield the crude 2-[(2-(2-methyl benzoyl)phenyl)-amino]-3-(4-hydroxyphenyl)-propionic acid methyl ester. The crude product is mixed with 250 ml of methanol and is refluxed for 30 min. After cooled to 0° C., the product is filtered, washed with methanol (2×50 ml), and dried under a vacuum to give the title compound (52.9 g, 34%).

EXAMPLE 28

Preparation of 2-[(2-(2-methylbenzoyl)phenyl)amino]-3-[4-(2-bromoethoxy)-phenyl]-propionic acid methyl ester

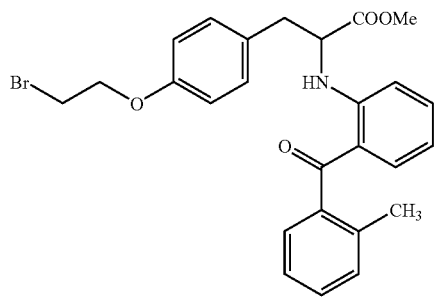

To a solution of potassium hydroxide (0.17 g, 2.95 mmol) in ethanol (20 ml) is added 2-[(2-(2-methylbenzoyl)phenyl)amino]-3-(4-hydroxyphenyl)-propionic acid methyl ester (1.15 g, 2.95 mmol) and 1,2-dibromoethane (5.54 g, 29.50 mmol). Then the mixture is heated to reflux for 8 hours. After cooled, the reaction mixture is filtered to remove the solid formed, and then the filtrate is evaporated under a vacuum. The crude product is purified by silica gel chromatography using hexane/EtOAc (4:1) as eluent to give the title compound (0.83 g, 57%).

EXAMPLE 29

Preparation of 2-[(2-(2-methylbenzoyl)phenyl)amino]-3-[4-(2-carbazolylethoxy)-phenyl]-propionic acid (Lab code CS01300110)

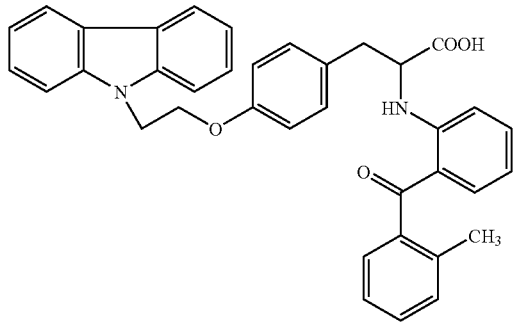

To a solution of 2-[(2-(2-methylbenzoyl)phenyl)amino]-3-[4-(2-bromoethoxy)-phenyl]-propionic acid methyl ester (0.24 g, 0.49 mmol) and carbazole (0.082 g, 0.49 mmol) in benzene (10 ml) is added tetrabutyl ammonium bromide (0.08 g) and 50% NaOH aqueous solution (0.084 g, 1.08 mmol), then the mixture is heated to reflux for 10 h. After cooled, benzene (30 ml) is added, and the mixture is washed with water (3×30 ml). Then the solvent is evaporated under a vacuum. The crude product is purified by silica gel chromatography using $CHCl_3$/MeOH (4:1) as eluent to give the title compound (0.11 g, 39%). HRMS calcd for $C_{37}H_{32}N_2O_4$: 568.6692. Found: 568.6689. MA calcd for $C_{37}H_{32}N_2O_4$: C, 78.15%; H, 5.67%; N, 4.93%. Found: C, 77.96%; H, 5.68%; N, 4.90%.

EXAMPLE 30

The example of compound 2-(1-methyl-3-oxo-3-phenyl-propenylamino)-3-[4-(2-carbazolylethoxy)-phenyl]-propionic acid (Compound CS-023), 2-((2-benzoylphenyl)amino)-3-[4-(2-carbazolylethoxy)-phenyl]-propionic acid (CS-0381), and 2-[(2-(4-fluorobenzoyl)phenyl)amino]-3-[4-(2-carbazolylethoxy)-phenyl]-propionic acid (CS-038) act as an RXR/PPARalpha heterodimer agonist in vitro. See, FIG. 1.

Activation of RXR/PPARalpha heterodimer by indicated compounds was measured by luciferase reporter assay. Briefly, full length PPARalpha was cloned by PCR using oligonucleotide primers (5'-acgtgcttcctgcttcataga-3' (SEQ ID NO: 1) and 5'-cctgagattagccacctccc-3' (SEQ ID NO:2)) from HepG2 cell. The amplified cDNA was cloned into an expression vector and sequenced. The reporter was constructed by insertion of an annealed oligonucleotide containing three copies of the PPAR response element (5'-gatcctctcctttgacctattgaactattacctacatttga-3' (SEQ ID NO:3)) to the upstream of the luceferase gene in pHD(X3)Luc vector. CV-1 cells were transfected in 96-well plates with the RXR and PPARalpha expression vectors together with the reporter construct. Cells were cultured in media containing the delipidized serum for 24 hours after transfection, then added with tested compounds and positive control WY (WY14643) dissolved in DMSO. The final concentration of DMSO in culture medium (200 ul) was 0.5%. Cells were treated with different compounds in different concentrations as indicated above for 24 hours, followed by luciferase assay in a plate reader (Fluoroscan, Thermo Life Sciences).

EXAMPLE 31

Figure 2:
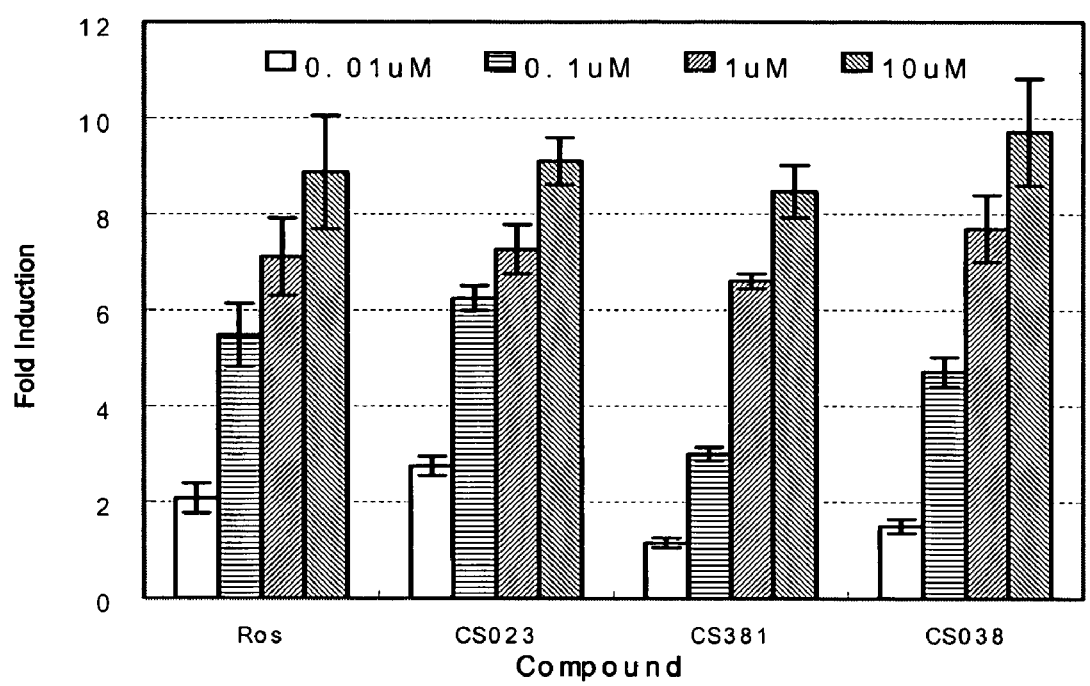
FIG. 2 shows comparative activation of RXR/PPAR gamma heterodimers by compounds of the present invention (Example 31).

The example of compound 2-(1-methyl-3-oxo-3-phenyl-propenylamino)-3-[4-(2-carbazolylethoxy)-phenyl]-propionic acid (Compound CS-023), 2-((2-benzoylphenyl)amino)-3-[4-(2-carbazolylethoxy)-phenyl]-propionic acid (CS-0381), and 2-[(2-(4-fluorobenzoyl)phenyl)amino]-3-[4-(2-carbazolylethoxy)-phenyl]-propionic acid (CS-038) act as an RXR/PPARgamma heterodimer agonist in vitro. See, FIG. 2.

Activation of RXR/PPARgamma heterodimer was measured by luciferase reporter assay. Briefly, full length PPARgamma was cloned by PCR using oligonucleotide primers (5'-ggggtacctgcttcagcagcgtgttcga-3' (SEQ ID NO:4) and 5'-gctctagatgttggcagtggctcaggac-3' (SEQ ID NO: 5)) from adipose tissue. The amplified cDNA was cloned into an expression vector and sequenced. The reporter was constructed by insertion of an annealed oligonucleotide containing 1 copy of the PPAR response element (5'-cgcgttcctttccgaacgtgacctttgtcctggtccccttttgct-3' (SEQ ID NO:6)) to the upstream of the luceferase gene. CV-1 cells were transfected in 96-well plates with the RXR and PPARgamma expression vectors together with the reporter construct. Cells were cultured in media containing the delipidized serum for 24 hours after transfection, then added with tested compounds and positive control Ros (Rosiglitazone) dissolved in DMSO. The final concentration of DMSO in culture medium (200 ul) was 0.5%. Cells were treated with different compounds in different concentrations as indicated above for 24 hours, followed by luciferase assay in a plate reader (Fluoroscan, Thermo Life Sciences).

EXAMPLE 32

Figure 3:
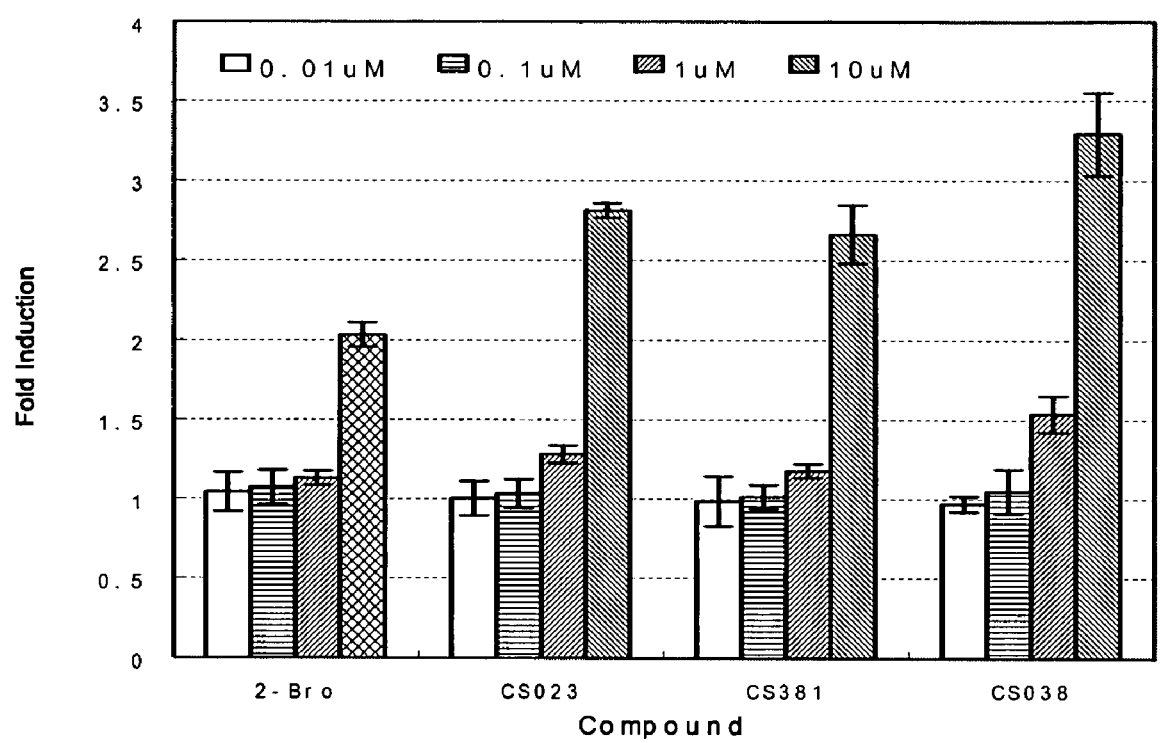
FIG. 3 graphically illustrates comparative activation of RXR/PPAR delta heterodimers by compounds of the present invention (Example 32).

The example of compound 2-(1-methyl-3-oxo-3-phenyl-propenylamino)-3-[4-(2-carbazolylethoxy)-phenyl]-propionic acid (Compound CS-023), 2-((2-benzoylphenyl)amino)-3-[4-(2-carbazolylethoxy)-phenyl]-propionic acid (CS-0381), and 2-[(2-(4-fluorobenzoyl)phenyl)amino]-3-[4-(2-carbazolylethoxy)-phenyl]-propionic acid (CS-038) act as an RXR/PPARdelta heterodimer agonist in vitro. See, FIG. 3.

Activation of RXR/PPARdelta heterodimer was measured by luciferase reporter assay. Briefly, full length PPARdelta was cloned by PCR using oligonucleotide primers (5'-ggggtacctgcttcagcagcgtgttcga-3' (SEQ ID NO:4) and 5'-gctctagatgttggcagtggctcaggac-3' (SEQ ID NO:5)) from adipose tissue. The amplified cDNA was cloned into an expression vector and sequenced. The reporter was constructed by insertion of an annealed oligonucleotide containing 1 copy of the PPAR response element (5'-cgcgttcctttccgaacgtgacctttgtcctggtccccttttgct-3' (SEQ ID NO:6)) to the upstream of the luceferase gene. CV-1 cells were transfected in 96-well plates with the RXR and PPARdelta expression vectors together with the reporter construct. Cells were cultured in media containing the delipidized serum for 24 hours after transfection, then added with tested compounds and positive control 2-Bro (2-Bromohexadecanoic acid) dissolved in DMSO. The final concentration of DMSO in culture medium (200 ul) was 0.5%. Cells were treated with different compounds in different concentrations as indicated above for 24 hours, followed by luciferase assay in a plate reader (Fluoroscan, Thermo Life Sciences).

EXAMPLE 33

Figure 4:
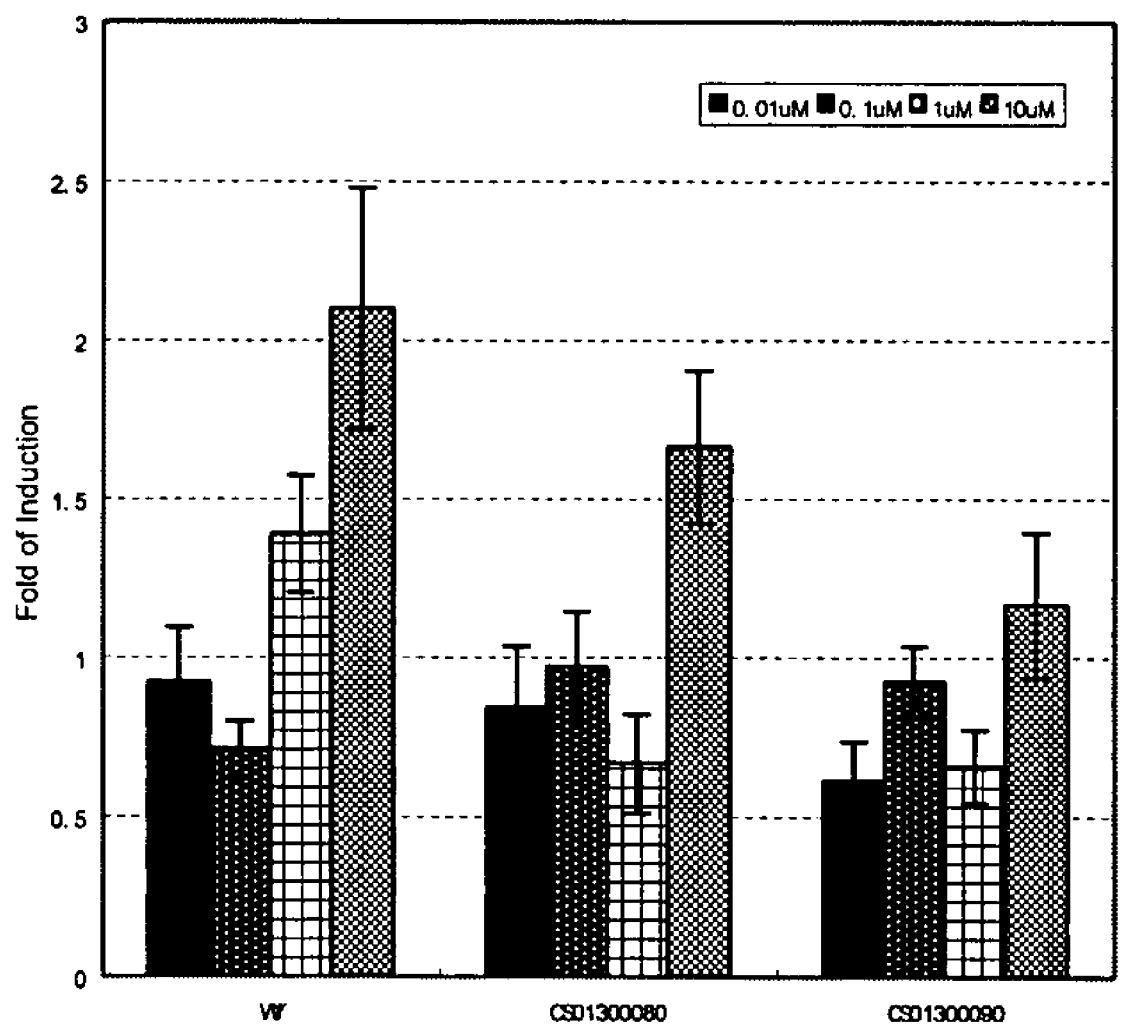
FIG. 4 shows comparative activation of RXR/PPAR alpha heterodimers by compounds of the present invention (Example 33).
Figure 5:
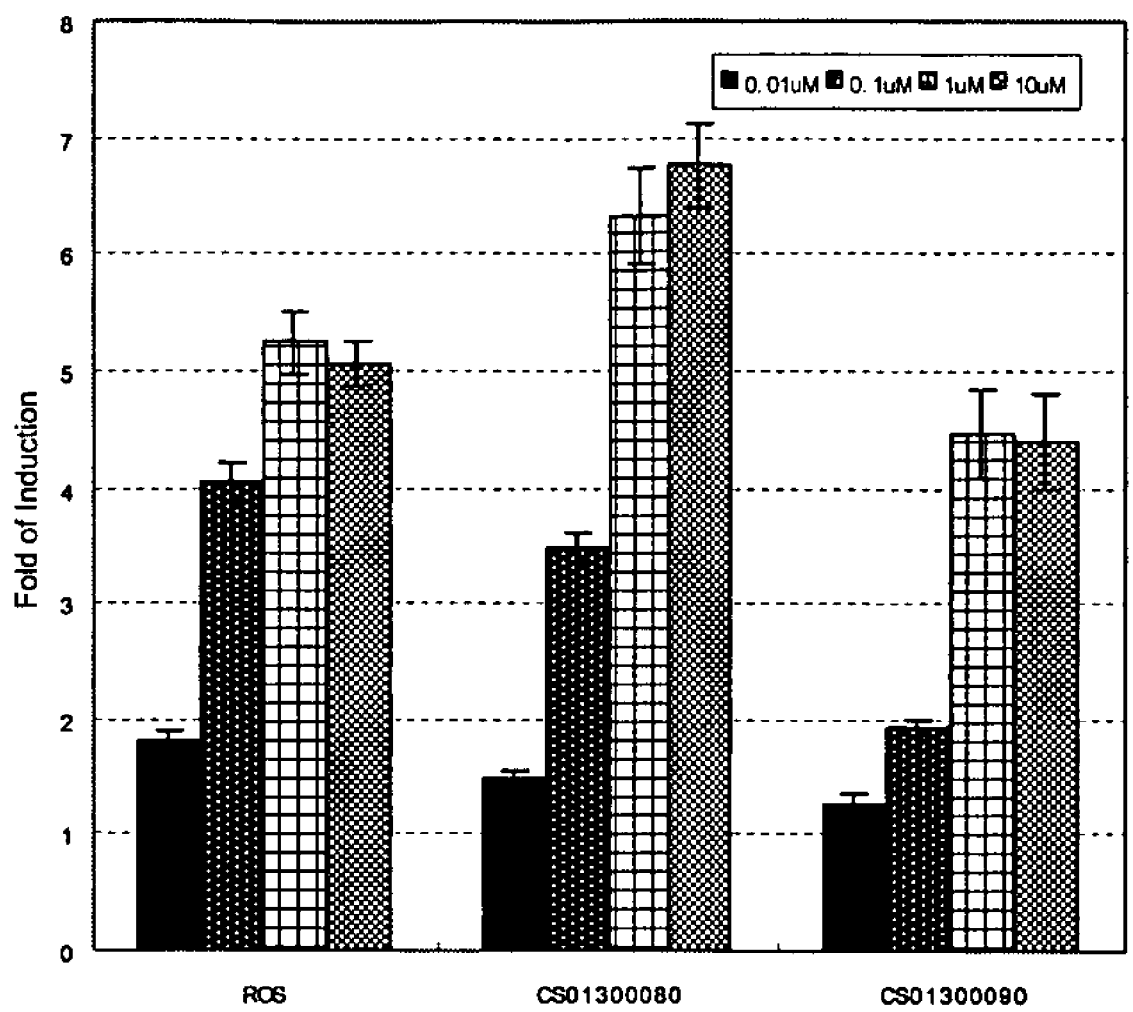
FIG. 5 shows comparative activation of RXR/PPAR gamma heterodimers by compounds of the present invention (Example 33).
Figure 6:
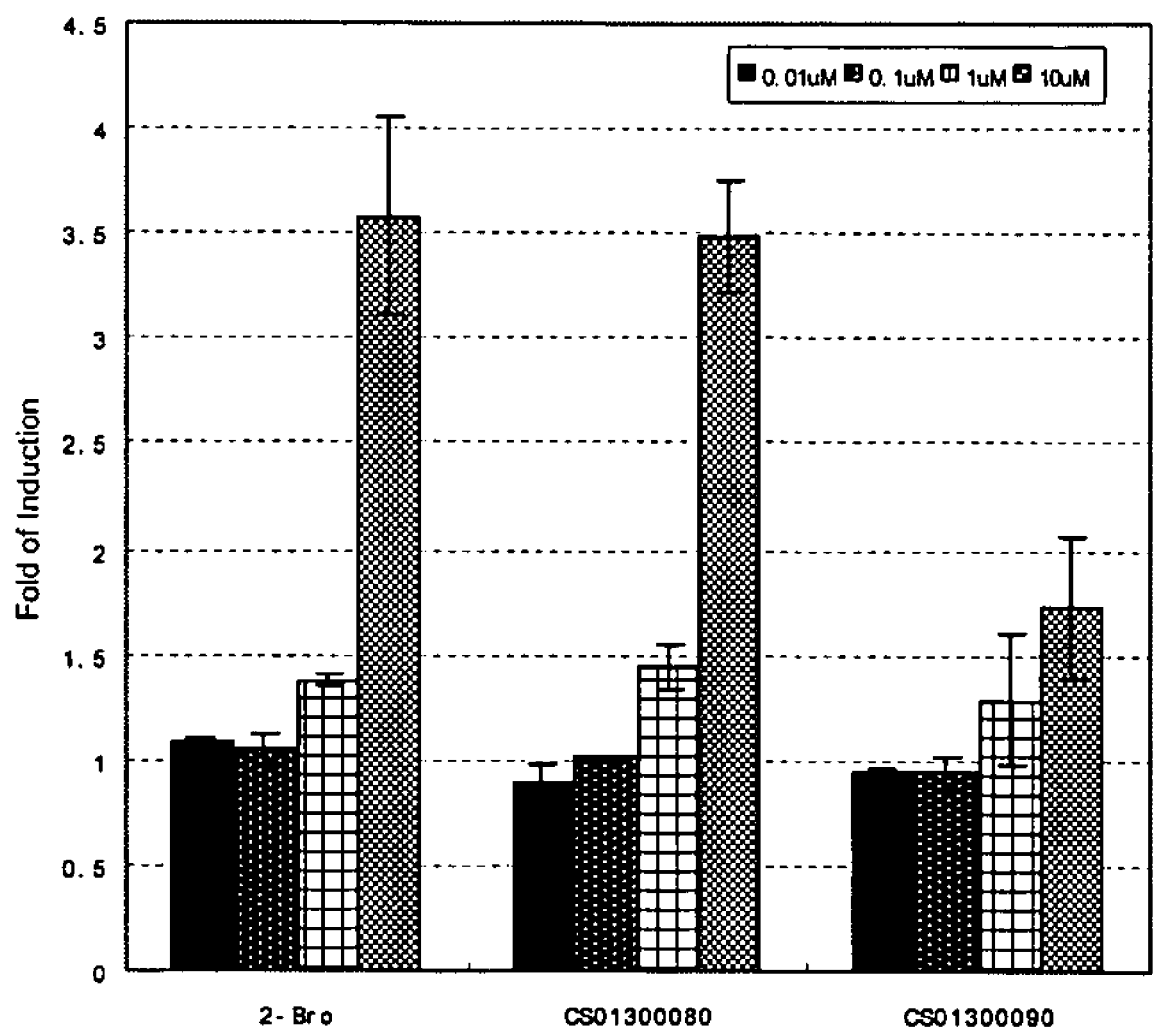
FIG. 6 shows comparative activation of RXR/PPAR delta heterodimers by compounds of the present invention (Example 33).

The example of compound 2-[(2-(4-methylbenzoyl)phenyl)amino]-3-[4-(2-carbazolylethoxy)-phenyl]-propionic acid (Lab code CS0130080), and 2-[(2-(4-tert-butylbenzoyl)phenyl)amino]-3-[4-(2-carbazolylethoxy)-phenyl]-propionic acid (Lab code CS0130090) act as RXR/PPAR heterodimers agonist in vitro. See, FIG. 4 (RXR/PPARalpha), FIG. 5 (RXR/PPARgamma), and FIG. 6 (RXR/PPARdelta).

EXAMPLE 34

Figure 7:
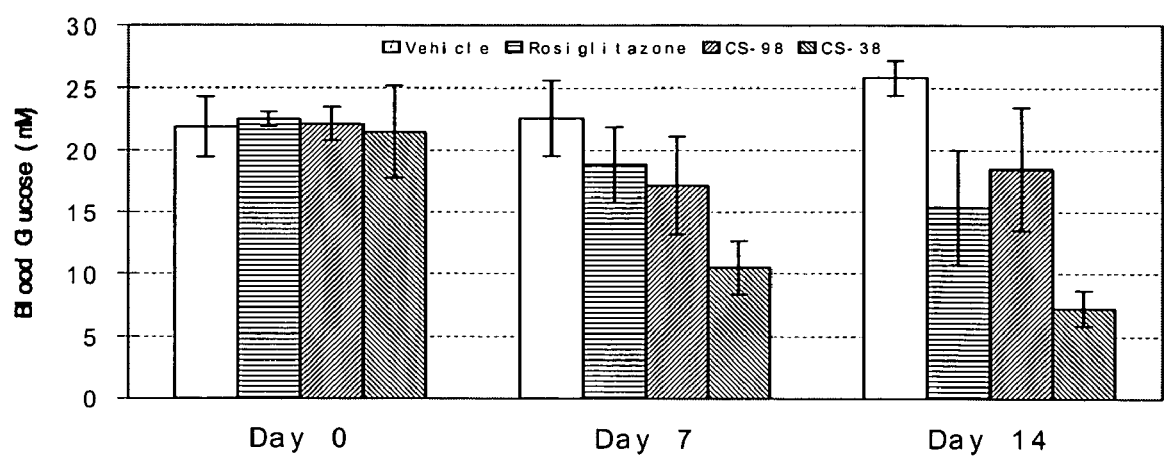
FIG. 7 graphically illustrates in vivo blood glucose lowering affected by a compound of the present invention (Example 34).

The example of compound 2-(1-methyl-3-oxo-3-phenyl-propenylamino)-3-[4-(2-carbazolylethoxy)-phenyl]-propionic acid (Compound CS-023, also named as CS-98 in the following figure), and 2-[(2-(4-fluorobenzoyl) phenyl)

amino]-3-[4-(2-carbazolylethoxy)-phenyl]-propionic acid (CS-038 at 30 mg/kg/bw and Rosiglitazone at 4 mg/kg/bw) lower blood glucose level in db/db mouse (animal number=10). See, FIG. 7.

EXAMPLE 35

Figure 8:
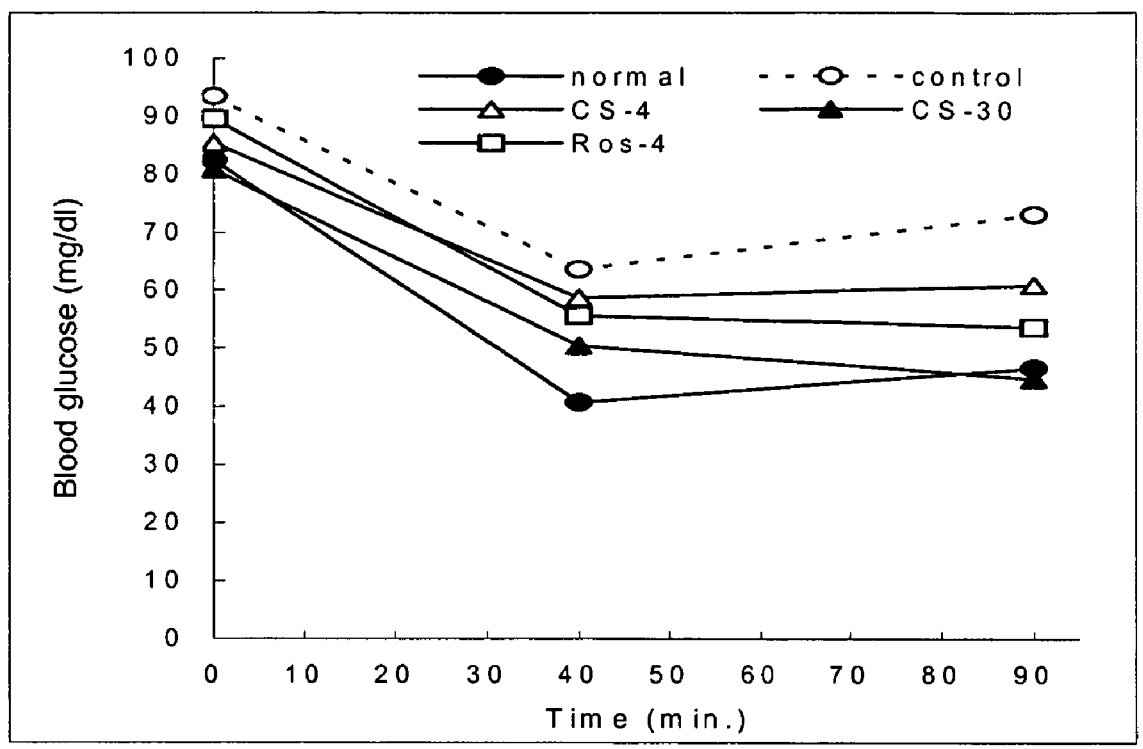
FIG. 8 graphically illustrates increased insulin sensitivity affected in vivo by a compound of the present invention (Example 35).

The example of treatment of experimental obese rat model by compound 2-[(2-(4-fluorobenzoyl)phenyl)amino]-3-[4-(2-carbazolylethoxy)-phenyl]-propionic acid (CS-038) increases insulin sensitivity in insulin tolerance test after 13-day drug treatment (doses indicated in following Figure as mg/kg/body weight, Ros means Rosiglitazone at 4 mg/kg/bw, CS-4 means CS-038 at 4 mg/kg/bw and CS-30 means CS-038 at 30 mg/kg/bw; Norma means lean rat; Control is obese rat and all treatments were carried out in obese rats; animal number=10). See, FIG. 8.

EXAMPLE 36

Figure 9:
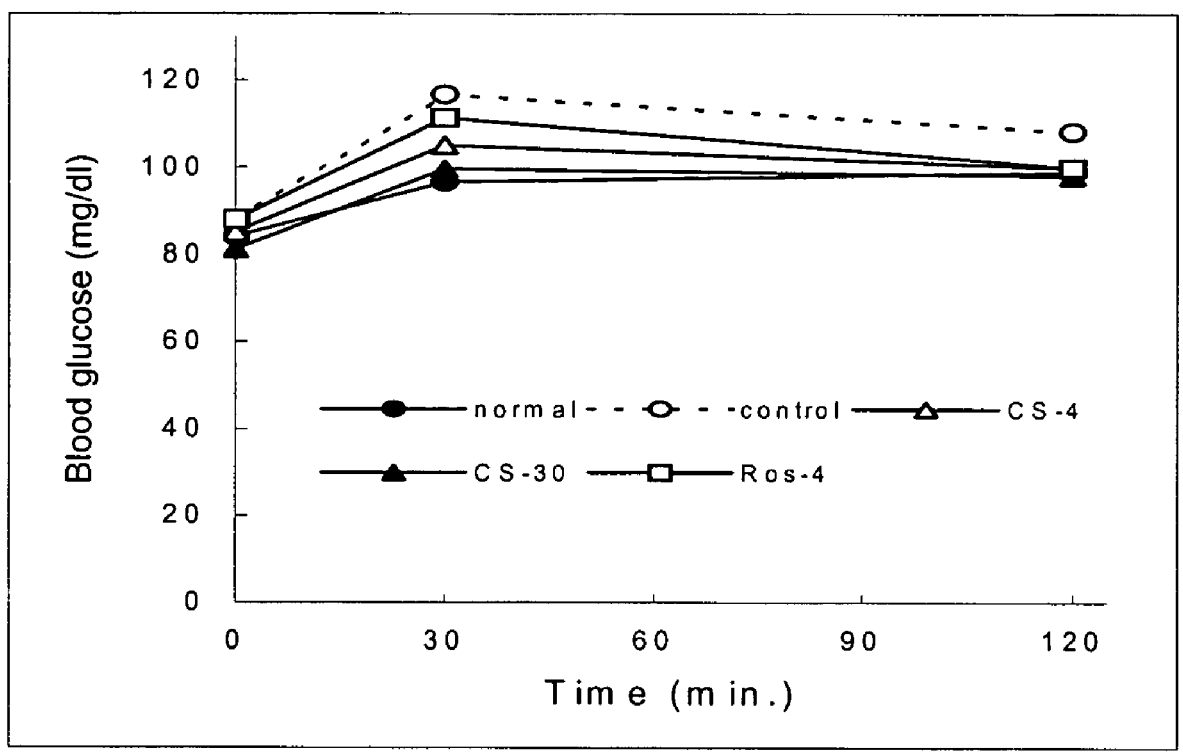
FIG. 9 graphically illustrates increased glucose tolerance affected in vivo by a compound of the present invention (Example 36).

The example of treatment of experimental obese rat model by compound 2-[(2-(4-fluorobenzoyl)phenyl)amino]-3-[4-(2-carbazolylethoxy)-phenyl]-propionic acid (CS-038) increases glucose tolerance in oral glucose tolerance test after 13-day drug treatment (doses indicated in following Figure as mg/kg/body weight, Ros means Rosiglitazone at 4 mg/kg/bw, CS-4 means CS-038 at 4 mg/kg/bw and CS-30 means CS-038 at 30 mg/kg/bw; Norma means lean rat; Control is obese rat and all treatments were carried out in obese rats; animal number=10). See, FIG. 9.

EXAMPLE 37

The example of treatment of experimental obese rats model by compound 2-[(2-(4-fluorobenzoyl)phenyl)amino]-3-[4-(2-carbazolylethoxy)-phenyl]-propionic acid (CS-038) lowers blood triglyceride after 13-day drug treatment (doses indicated in FIG. as mg/kg/body weight; Norma means lean rat; Control is obese rat and all treatments were carried out in obese rats; animal number=10).

TABLE 1

| Animal Group | Dose (mg/kg) | Triglyceride (mg/dl) | Cholesterol (mg/dl) |
|---|---|---|---|
| Normal | — | 149.6 ± 39.8* | 73.1 ± 7.8** |
| Control | — | 233.9 ± 101.6 | 109.4 ± 26.7 |
| CS038 | 4 | 150.3 ± 52.1* | 98.4 ± 29.4 |
| CS038 | 30 | 143.2 ± 61.8* | 86.6 ± 37.7 |
| Ros | 4 | 273.3 ± 87.4 | 112.7 ± 25.5 |

Compared with the Normal group: $*P < 0.05$, $**P < 0.01$

EXAMPLE 38

The example of treatment of experimental obese rats mode by compound 2-[(2-(4-fluorobenzoyl)phenyl)amino]-3-[4-(2-carbazolylethoxy)-phenyl]-propionic acid (CS-038) does not induce body weight and abdomen fat increases after 15-day drug treatment (doses indicated in following Figure as mg/kg/body weight; Control is obese rat and all treatments were carried out in obese rats; animal number=10).

TABLE 2

| Animal Group | Dose (mg/kg) | Body Weight (g) | | | | Abdomen Fat Weight (g) |
|---|---|---|---|---|---|---|
| | | 0 day | 6 days | 9 days | 15 days | |
| Con | — | 576.5 ± 138.0 | 569.4 ± 142.1 | 568.5 ± 145.3 | 562.7 ± 136.5 | 60.4 ± 21.0 |
| CS038 | 4 | 591.5 ± 130.0 | 580.8 ± 130.2 | 575.2 ± 130.6 | 569.4 ± 122.9 | 55.8 ± 16.8 |
| CS038 | 30 | 580.5 ± 134.9 | 586.1 ± 143.2 | 586.5 ± 144.2 | 578.3 ± 176.8 | 56.6 ± 21.1 |
| Ros | 4 | 594.9 ± 169.3 | 604.5 ± 181.4 | 601.6 ± 183.9 | 596.4 ± 176.8 | 63.1 ± 31.4 |

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described compositions and modes for carrying out the invention which are obvious to those skilled in the art or related fields are intended to be within the scope of the following claims.

What is claimed is:

1. An isolated compound of Formula I

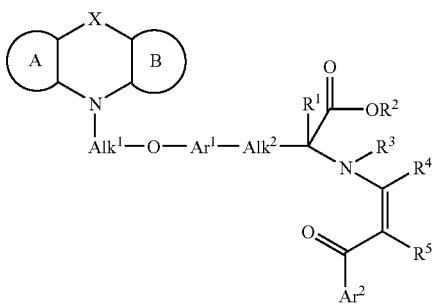

wherein
ring A and ring B, fused to the ring containing X and N, independently of each other represents a benzene ring, which may optionally substituted with one or more halogen, hydroxy, nitro, cyano, alkyl, alkenyl, aralkyl, heteroarylalkyl, aminoalkyl, alkoxyalkyl aryloxyalkyl, aralkoxyalkyl, hydroxyalkyl, thioalkyl, heterocyclyl, alkoxy, aryl, aryloxy, aralkoxy, heteroaryl, heteroaryloxy, heteroaralkoxy, acyl, acyloxy, amino, alkylamino, arylamino, or aralkylamino;
X is a valence bond;
$R^1$ is H, alkyl, alkenyl, aralkyl, heteroarylalkyl, aminoalkyl, alkoxyalkyl, aryloxyalkyl, aralkoxyalkyl, hydroxyalkyl, thioalkyl, heterocyclyl, OH, halogen, alkoxy, aryl, aryloxy, aralkoxy, heteroaryl, heteroaryloxy, heteroaralkoxy, acyl, acyloxy, amino, alkylamino, arylamino, or aralkylamino;
$R^2$ is H, alkyl, alkenyl, aralkyl, heteroarylalkyl, heterocyclyl, aryl, or heteroaryl;
$R^3$ is H, alkyl, alkenyl, aralkyl, heteroarylalkyl, heterocyclyl, aryl, or heteroaryl;
$R^4$ and $R^5$ are independently H, alkyl, alkenyl, aralkyl, heteroarylalkyl, aminoalkyl, alkoxyalkyl, aryloxyalkyl, aralkoxyalkyl, hydroxyalkyl, thioalkyl, heterocyclyl, OH, halogen, alkoxy, aryl, aryloxy, aralkoxy, heteroaryl, heteroaryloxy, heteroaralkoxy, acyl, acyloxy, amino, alkylamino, arylamino, or aralkylamino; $R^4$ and $R^5$ may form a 5 or 6 membered ring optionally substituted with one or more halogen, hydroxy, nitro, cyano, alkyl, alkenyl, aralkyl, heteroarylalkyl, aminoalkyl, alkoxyalkyl, aryloxyalkyl, aralkoxyalkyl, hydroxyalkyl, thioalkyl, heterocyclyl, alkoxy, aryl, aryloxy, aralkoxy, heteroaryl, heteroaryloxy, heteroaralkoxy, acyl, acyloxy, amino, alkylamino, arylamino, or aralkylamino;
$Alk^1$ represents $C_{1-6}$alkylene;
$Alk^2$ represents $C_{1-2}$alkylene;
$Ar^1$ represents arylene, hetero arylene, or a divalent heterocyclic group optionally substituted with one or more halogen, $C_{1-6}$alkyl, amino, hydroxy, $C_{1-6}$alkoxyl or aryl;
$Ar^2$ represents a substituted aryl group with one or more substituents independently selected from halogen, $C_{1-6}$alkyl, amino, hydroxy, $C_{1-6}$alkoxyl or aryl; a hetero aryl, or a heterocyclic group optionally substituted with one or more halogen, $C_{1-6}$alkyl, amino, hydroxy, $C_{1-6}$alkoxyl or aryl.

2. A compound according to claim 1, wherein
ring A is a benzene ring;
ring B is a benzene ring;
X is a valence bond;
$R^1$ is H or alkyl;
$R^2$ is H or alkyl;
$R^3$ is H or alkyl;
$R^4$ and $R^5$ are independently H or alkyl;
$Alk^1$ is $C_{2-3}$alkylene;
$Alk^2$ is $C_{1-2}$alkylene;
$Ar^1$ is an arylene group; and,
$Ar^2$ is a substituted aryl group.

3. A compound according to claim 1, wherein
ring A is a benzene ring;
ring B is a benzene ring;
X is a valence bond;
$R^1$ is H or alkyl;
$R^2$ is H or alkyl;
$R^3$ is H or alkyl;
$R^4$ and $R^5$ form a 6 membered aromatic ring;
$Alk^1$ is $C_{2-3}$alkylene;
$Alk^2$ is $C_{1-2}$alkylene;
$Ar^1$ is 6 membered aromatic ring; and,
$Ar^2$ is a substituted aryl group.

4. A compound according to claim 1, wherein
ring A is a benzene ring;
ring B is a benzene ring;
X is a valence bond;
$R^1$ is H;
$R^2$ is H;
$R^3$ is H;
$R^4$ is methyl; $R^5$ is H;
$Alk^1$ is $CH_2CH_2$;
$Alk^2$ is $CH_2$;
$Ar^1$ is benzene ring;
$Ar^2$ is a substituted benzene ring with one or more fluorine.

5. A compound according to claim 1, wherein
ring A is a benzene ring;
ring B is a benzene ring;
X is a valence bond;
$R^1$ is H;
$R^2$ is H;
$R^3$ is H;
$R^4$ and $R^5$ form a benzene ring;
$Alk^1$ is $CH_2CH_2$;
$Alk^2$ is $CH_2$;
$Ar^1$ is benzene ring;
$Ar^2$ is a substituted benzene ring with one or more fluorine.

6. A compound according to claim 1, wherein
ring A is a benzene ring;
ring B is a benzene ring;
X is a valence bond;
$R^1$ is H;
$R^2$ is H;
$R^3$ is H;
$R^4$ is methyl; $R^5$ is H;
$Alk^1$ is $CH_2CH_2$;
$Alk^2$ is $CH_2$;
$Ar^1$ is benzene ring;
$Ar^2$ is pyridine ring substituted with none, one or more halogen.

7. A compound according to claim 1, wherein
ring A is a benzene ring;
ring B is a benzene ring;
X is a valence bond;
$R^1$ is H;
$R^2$ is H;
$R^3$ is H;
$R^4$ and $R^5$ form a benzene ring;
$Alk^1$ is $CH_2CH_2$;
$Alk^2$ is $CH_2$;

$Ar^1$ is benzene ring;

$Ar^2$ is pyridine ring substituted with none, one or more fluorine.

8. A process for the preparation of a compound of Formula I

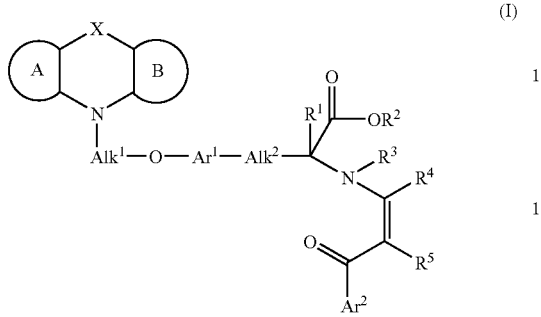

wherein
  ring A and ring B, fused to the ring containing X and N, independently of each other represents a benzene ring, which may optionally substituted with one or more halogen, hydroxy, nitro, cyano, alkyl, alkenyl, aralkyl, heteroarylalkyl, aminoalkyl, alkoxyalkyl, aryloxyalkyl, aralkoxyalkyl, hydroxyalkyl, thioalkyl, heterocyclyl, alkoxy, aryl, aryloxy, aralkoxy, heteroaryl, heteroaryloxy, heteroaralkoxy, acyl, acyloxy, amino, alkylamino, arylamino, or aralkylamino;

X is a valence bond;

$R^1$ is H, alkyl, alkenyl, aralkyl, heteroarylalkyl, aminoalkyl, alkoxyalkyl, aryloxyalkyl, aralkoxyalkyl, hydroxyalkyl, thioalkyl, heterocyclyl, OH, halogen, alkoxy, aryl, aryloxy, aralkoxy, heteroaryl, heteroaryloxy, heteroaralkoxy, acyl, acyloxy, amino, alkylamino, arylamino, or aralkylamino;

$R^2$ is H, alkyl, alkenyl, aralkyl, heteroarylalkyl, heterocyclyl, aryl, or heteroaryl;

$R^3$ is H, alkyl, alkenyl, aralkyl, heteroarylalkyl, heterocyclyl, aryl, or heteroaryl;

$R^4$ and R5 are independently H, alkyl, alkenyl, aralkyl, heteroarylalkyl, aminoalkyl, alkoxyalkyl, aryloxyalkyl, aralkoxyalkyl, hydroxyalkyl, thioalkyl, heterocyclyl, OH, halogen, alkoxy, aryl, aryloxy, aralkoxy, heteroaryl, heteroaryloxy, heteroaralkoxy, acyl, acyloxy, amino, alkylamino, arylamino, or aralkylamino; $R^4$ and $R^5$ may form a 5 or 6 membered ring optionally substituted with one or more halogen, hydroxy, nitro, cyano, alkyl, alkenyl, aralkyl, heteroarylalkyl, aminoalkyl, alkoxyalkyl, aryloxyalkyl, aralkoxyalkyl, hydroxyalkyl, thioalkyl, heterocyclyl, alkoxy, aryl, aryloxy, aralkoxy, heteroaryl, heteroaryloxy, heteroaralkoxy, acyl, acyloxy, amino, alkylamino, arylamino, or aralkylamino;

$Alk^1$ represents $C_{1-6}$alkylene;

$Alk^2$ represents $C_{1-2}$alkylene;

$Ar^1$ represents arylene, hetero arylene, or a divalent heterocyclic group optionally substituted with one or more halogen, $C_{1-6}$alkyl, amino, hydroxy, $C_{1-6}$alkoxyl or aryl;

$Ar^2$ represents a substituted aryl group with one or more substituents independently selected from halogen, $C_{1-6}$alkyl, amino, hydroxy, $C_{1-6}$alkoxyl or aryl; a hetero aryl, or a heterocyclic group optionally substituted with one or more halogen, $C_{1-6}$alkyl, amino, hydroxy, $C_{1-6}$alkoxyl or aryl, a stereoisomer, enantiomer, diastereomer, hydrate or pharmaceutically acceptable salts thereof comprising the steps of:

a) initiating a condensation reaction between compound 1 and β-diketone 2 to give the vinylogous amide analogues 3;

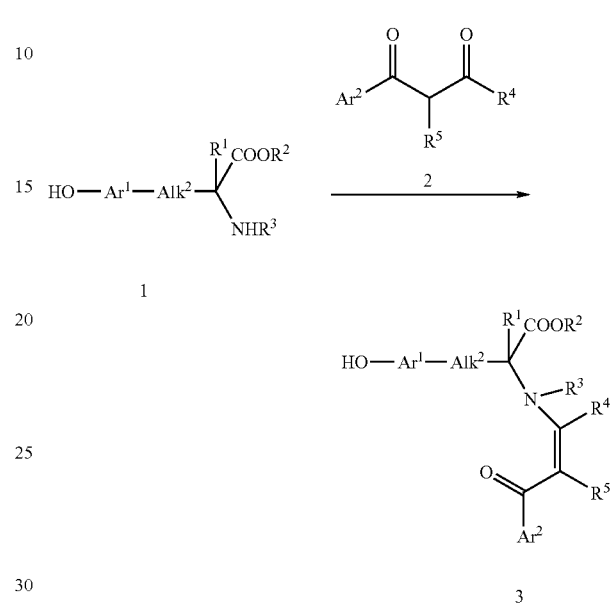

b) performing O-Alkylation of 3 to gave compound 4;

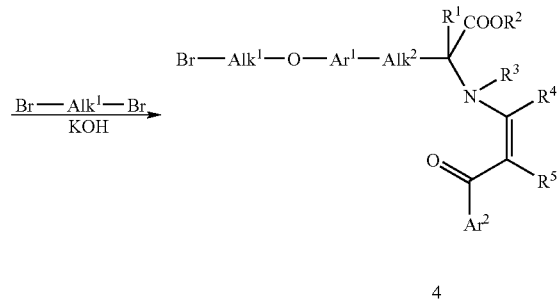

c) performing N-Alkylation of 4 gave the substituted arylalcanoic acid derivatives 6

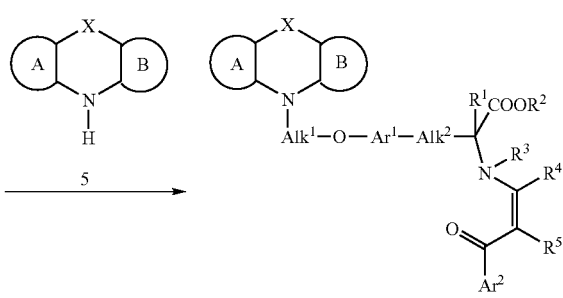

9. A process according to claim 8 wherein:
(a) the condensation reaction is carried out in ethanol at reflux temperature;
(b) the O-alkylation is achieved by treatment of 3 with KOH and dibromoalkane in ethanol;
(c) the N-alkylation is achieved by treating compound 4 with NaOH and compound 5 in the presence of tetrabutyl ammonium bromide.

10. A pharmaceutical composition comprising an effective amount of a
compound according to claim 1 or its pharmaceutically acceptable salt and at least one pharmaceutically acceptable carrier or diluent.

11. The pharmaceutical composition according to claim 10 in unit dosage form, comprising from about 0.05 to about 200 mg of the compound.

12. The pharmaceutical composition according to claim 11 which is suitable for administration by an oral, nasal, transdermal, pulmonary, or parenteral route.

13. A method of treatment of type 2 diabetes comprising administering to a subject in need thereof an effective amount of a compound according to claim 1.

14. A method of treatment of at least one condition selected from the group consisting of type 1 diabetes, type 2 diabetes, dyslipidemia, syndrome X, cardiovascular disease, atherosclerosis, hypercholesteremia, and obesity, comprising administering to a subject in need thereof an effective amount of a compound according to claim 1.

15. The method according to claim 14, wherein the effective amount of the compound is in the range of from about 0.05 to about 200 mg/kg body weight per day.

* * * * *